United States Patent [19]

Yabuki et al.

[11] Patent Number: 4,981,965

[45] Date of Patent: Jan. 1, 1991

[54] PROCESS FOR FORMATION OF BASE

[75] Inventors: Yoshiharu Yabuki; Jiro Tsukahara; Taku Nakamura, all of Kanagawa, Japan

[73] Assignee: Fuji Photo Film Co., Ltd., Kanagawa, Japan

[21] Appl. No.: 242,406

[22] Filed: Sep. 9, 1988

[30] Foreign Application Priority Data

Sep. 9, 1987 [JP] Japan ............................... 62-226134
Sep. 9, 1987 [JP] Japan ............................... 62-226135

[51] Int. Cl.$^5$ .................. C07C 257/14; C07D 213/74; C07D 233/88; C07D 251/54

[52] U.S. Cl. .................................... 544/196; 544/402; 546/306; 548/316; 564/236

[58] Field of Search ................ 564/236; 544/402, 196; 546/306; 548/316

[56] References Cited

U.S. PATENT DOCUMENTS

| | | | |
|---|---|---|---|
| 3,493,374 | 2/1970 | Roncken et al. | 430/159 |
| 4,060,420 | 11/1977 | Merkel et al. | 96/114.1 |
| 4,560,763 | 12/1985 | Sato et al. | 546/341 |
| 4,897,335 | 1/1990 | Kakimi | 330/138 |

FOREIGN PATENT DOCUMENTS

| | | |
|---|---|---|
| 0160996 | 11/1985 | European Pat. Off. . |
| 0234580 | 9/1987 | European Pat. Off. . |
| 221477 | 4/1985 | Fed. Rep. of Germany . |
| 1580688 | 9/1969 | France . |
| 2272645 | 12/1975 | France . |
| 57-125091 | 8/1982 | Japan . |
| 59-180537 | 10/1984 | Japan . |
| 61-51139 | 3/1986 | Japan . |
| 998949 | 7/1965 | United Kingdom . |

OTHER PUBLICATIONS

Abstract of Japanese Pat. Prov'l Publication No. 57 (1982)-125,091.

*Primary Examiner*—Richard L. Raymond
*Attorney, Agent, or Firm*—Sughrue, Mion, Zinn, Macpeak & Seas

[57] ABSTRACT

A base precursor in the form of a salt of an organic base with a carboxylic acid is disclosed. The organic base is a diacidic to tetraacidic base which is composed of two to four guanidine moieties and at least one linking group for the guanidine moities. The organic base is such a hydrophilic compound that the number of carbon atoms contained in the organic base is not more than six times the number of the guanidine moieties. The linking group is a residue of a hydrocarbon or a heterocyclic ring. The guanidine moiety corresponds to an atomic group formed by removing one or two hydrogen atoms from a compound having the following formula (I):

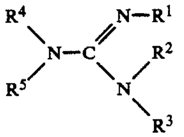

(I)

where each of $R^1$, $R^2$, $R^3$, $R^4$ and $R^5$ independently is hydrogen, an alkyl group, an alkenyl group, an alkynyl group, a cycloalkyl group, an aralkyl group, an aryl group or a heterocyclic group, each of which may have one or more substituent groups, and any two of $R^1$, $R^2$, $R^3$, $R^4$ and $R^5$ may be combined together to form a five-membered or six-membered nitrogen-containing heterocyclic ring. A process for formation of an organic base from the base precursor and a light-sensitive material containing the base precursor are also disclosed.

12 Claims, 6 Drawing Sheets

PROCESS FOR FORMATION OF BASE

FIELD OF THE INVENTION

The present invention relates to a base precursor in the form of a salt of an organic base with a carboxylic acid. The invention also relates to a process for formation of an organic base from the base precursor and to a light-sensitive material containing the base precursor.

BACKGROUND OF THE INVENTION

Bases are reagents which are widely used for various reactions such as hydrolysis reactions, polymerization reactions, color reactions, redox reactions, neutralization reactions, etc. For example, various recording materials such as silver salt photographic materials and diazotype photographic materials require a base during an image forming process.

An image may be formed on a recording material by a wet developing process using a treating solution (developing solution) or a dry developing process (e.g., heat developing process). A base may be contained in the developing solution, when an image is formed by the wet process such as a developing process. On the other hand, when an image is formed by a dry process, the base is previously incorporated into a recording material. However, the base incorporated into the recording material sometimes causes a problem with respect to the stability of the recording material. For example, the base may adversely affected the other ingredients in the recording material or the base itself may be deteriorated during the storage of the recording material.

In order to eliminate the above-mentioned problem, it has been proposed to use a base precursor in place of the base. The base precursor is a neutral or weakly basic compound and can form a base during the image forming process. In a heat developable recording material, a heat decomposition type base precursor is preferably used. Various kinds of the heat decomposition type base precursors have been studied and proposed. A typical example of the heat decomposition type base precursor is a salt of an organic base with a carboxylic acid. The base precursors in the form of a salt of an organic base with a carboxylic acid are described in U.S. Pat. No. 3,493,374 (triazine compound and carboxylic acid), U.K. Pat. No. 998,949 (trichloroacetate), Japanese Patent Provisional Publication No. 59(1984)-180537 (propiolate), and Japanese Patent Provisional Publication No. 61(1986)-51139 and U.S. Pat. No. 4,060,420 (sulfonylacetate). These base precursors release a base when the carboxyl group in the carboxylic acid undergoes decarboxylation at an elevated temperature.

It has been demanded to find out a base precursor which is stable during storage but is quickly decomposed to form a base when it is heated. In the above-mentioned publications, a prime attention is paid to a decarboxylation of the carboxyl group of the carboxylic acid, and the carboxylic acid is mainly studied.

However, these base precursors do not fully meet both of the two demands for stability during storage and for quick base formation.

SUMMARY OF THE INVENTION

It is an object of the present invention to provide a base precursor which is very stable during storage (at room temperature) and rapidly releases a base when it is heated.

There is provided by the present invention a base precursor in the form of a salt of an organic base with a carboxylic acid, wherein the organic base is a diacidic to tetraacidic base which is composed of two or four guanidine moieties and at least one residue of a hydrocarbon or a heterocyclic ring as a linking group for the guanidine moieties, the number of carbon atoms contained in said organic base being not more than six times the number of the guanidine moieties, and said guanidine moiety corresponding to an atomic group formed by removing one or two hydrogen atoms from a compound having the following formula (I):

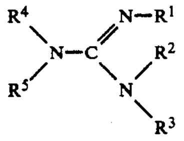

(I)

wherein each of $R^1$, $R^2$, $R^3$, $R^4$ and $R^5$ independently is a monovalent group selected from the group consisting of hydrogen, an alkyl group, an alkenyl group, an alkynyl group, a cycloalkyl group, an aralkyl group, an aryl group and a heterocyclic group, and any two of $R^1$, $R^2$, $R^3$, $R^4$ and $R^5$ may be combined together to form a five-membered or six-membered nitrogen-containing heterocyclic ring.

There is also provided by the invention a process for formation of a base comprising a step of heating a base precursor in the form of a salt of an organic base with a carboxylic acid, wherein the organic base of the base precursor which is composed of two to four guanidine moieties and at least one residue of a hydrocarbon or a heterocyclic ring as a linking group for the guanidine moieties, the number of carbon atoms contained in said organic base being not more than six times the number of the guanidine moieties, and said guanidine moiety corresponding to an atomic group formed by removing one or two hydrogen atoms from a compound having the formula (I).

The base precursor of the present invention is advantageously used in a light-sensitive material comprising a support and a light-sensitive layer which contains silver halide, a reducing agent and an ethylenic unsaturated polymerizable compound.

The base precursor of the present invention is characterized in that the organic base has two to four guanidine moieties derived from the compound (guanidine or a guanidine derivative) having the formula (I).

The present inventors have noted that in order to improve a base precorsor composed of a carboxylic acid and an organic base, a prime attention should be paid to the organic base rather than the carboxylic acid. According to study of the inventors, there has been discovered a base precursor which satisfactorily functions when the diacidic to tetraacidic base described above is used as the organic base. The obtained base precursor is very stable during storage and rapidly releases a base at an elevated temperature. This surprising effect is explained below.

The salt composed of a diacidic, triacidic or tetraacidic base with a carboxylic acid has a stable crystal structure, compared with a salt wherein the organic base is a monoacidic base. Particularly, when the diacidic to tetraacidic base has a symmetrical structure, the crystal structure is highly stable.

Further, according to the present invention, the organic base is such a hydrophilic compound that the number of carbon atoms contained in the organic base is not more than six times the number of the guanidine moieties. The present inventors have found that the above-defined hydrophilic organic base forms a strong ion pair with a carboxylic acid. Accordingly, the base precursor of the present invention has a very stable crystal structure.

Furthermore, a functional group accelerating decarboxylation such as an aryl group is often introduced into the carboxylic acid of the base precursor. Consequently, the carboxylic acid generally has a hydrophobic residue. In a salt composed of the carboxylic acid having a hydrophobic residue and the diacidic to tetraacidic base, a plurality of the hydrophobic residue in the carboxylic acid are positioned around the organic base through ionic bonds. Accordingly, the base is located in the center of the salt surrounded by the hydrophobic residues of the carboxylic acid. The above-mentioned structure is much stable as compared with the structure of a salt wherein the organic base is a monoacidic base, where the organic base and the hydrophobic residue in the carboxylic acid are positioned at both ends of the structure through ionic bond.

The present inventors have found that the base precursor composed of a carboxylic acid and an organic base melts or is dissolved in a binder contained in a recording material at an elevated temperature and then the decarboxylation of the carboxylic acid is initiated. The base precursor of the present invention has a stable crystal structure as mentioned above. Accordingly, the crystal structure of the base precursor is kept until it melts or is dissolved at an elevated temperature. Therefore, the carboxylic acid is rapidly decarboxylated to release a base at the same time that the crystal structure is broken.

When the carboxylic acid has hydrophobic residues, the carboxyl group of the carboxylic acid and the organic base are blocked by the hydrophobic residues in the base precursor of the present invention. Accordingly, the base precursor is prevented by the hydrophobic residue from being dissovled in a binder (which generally is hydrophilic). The crystal structure of the salt is further stabilized by intermolecular interaction between the hydrophobic residues. Therefore, the base precursor of the present invention exhibits much higher stability during storage when the carboxylic acid has the hydrophobic residues.

The diacidic to tetraacidic base derived from a compound (guanidine or a guanidien derivative) having the formula (I) is used as the organic base in the base precursor of the present invention. Accordingly, the base precursor of the present invention releases the guanidine derivative, which is a strong base, so that the released base strongly functions in various systems requiring a base such as a recording material.

DETAILED DESCRIPTION OF THE INVENTION

Figure 1:
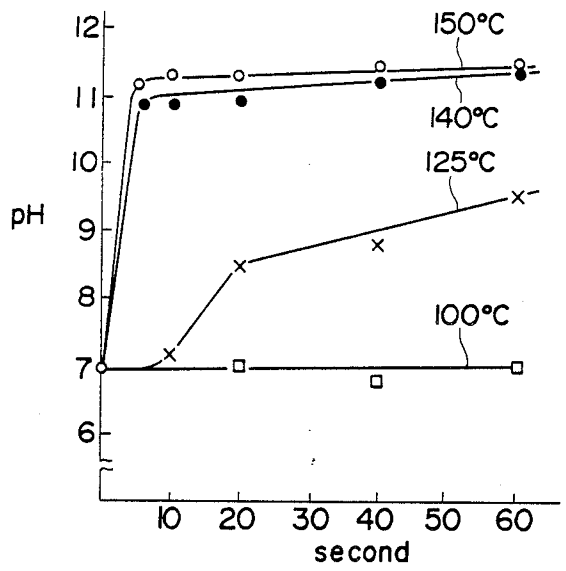
FIG. 1 to 10 are graphs showing the results of the measurements of changes in the pH of the samples during heating, wherein the abscissa axis represents the heating time and the ordinate axis represents the pH.
Figure 2:
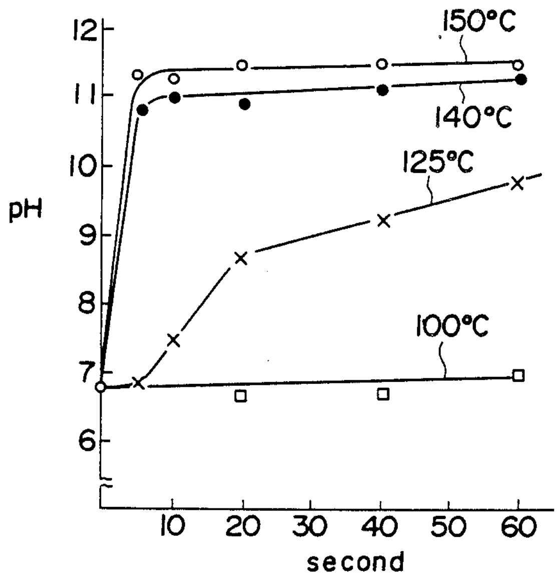
Figure 3:
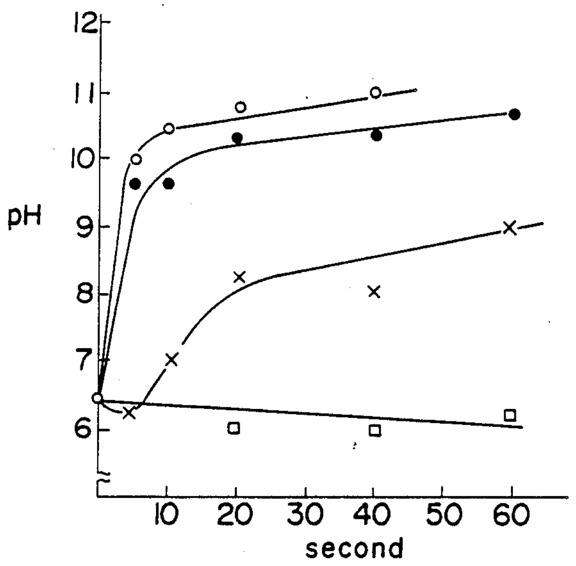
Figure 4:
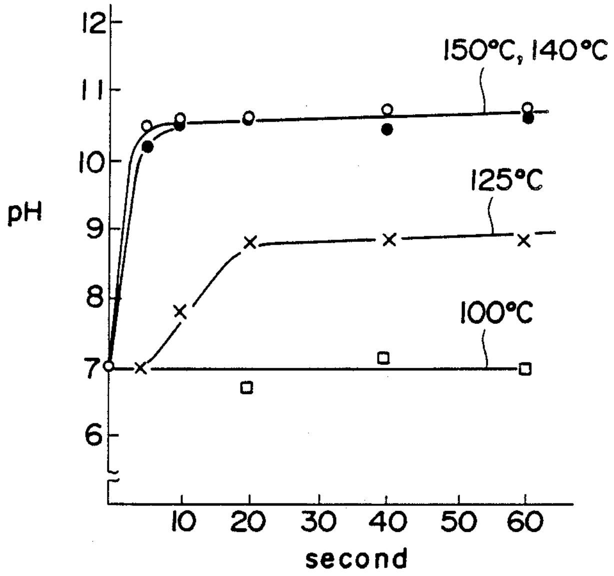
Figure 5:
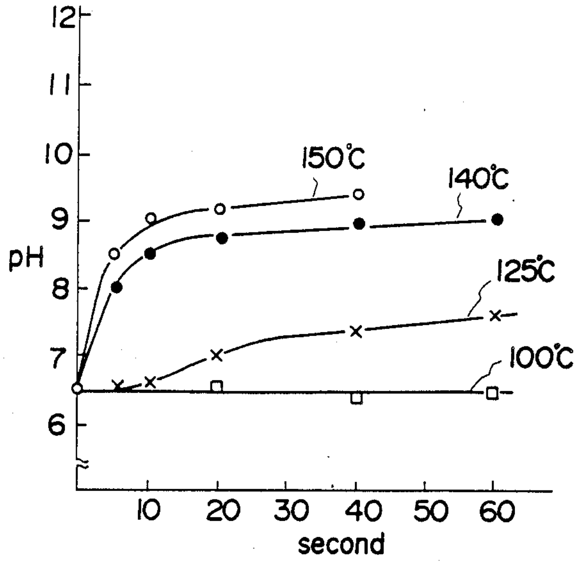
Figure 6:
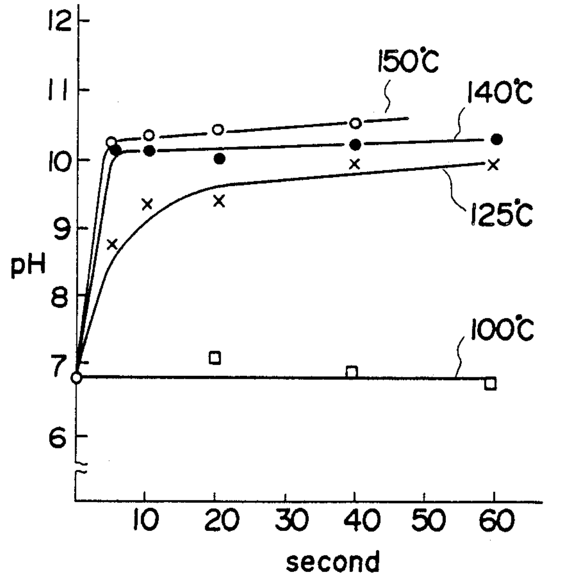
Figure 7:
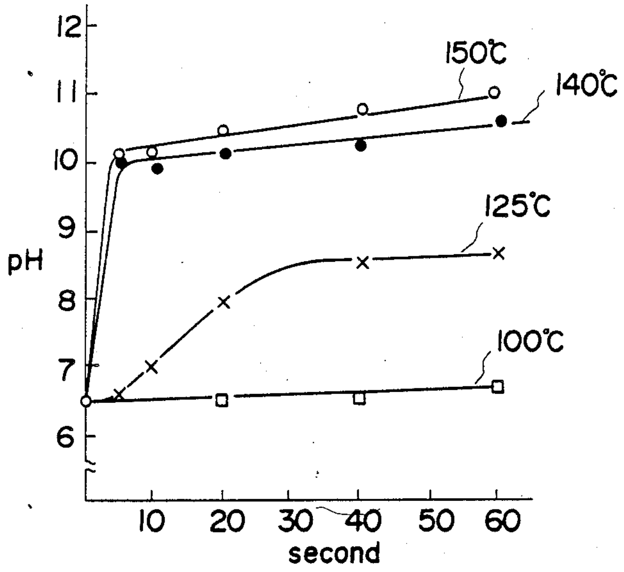
Figure 8:
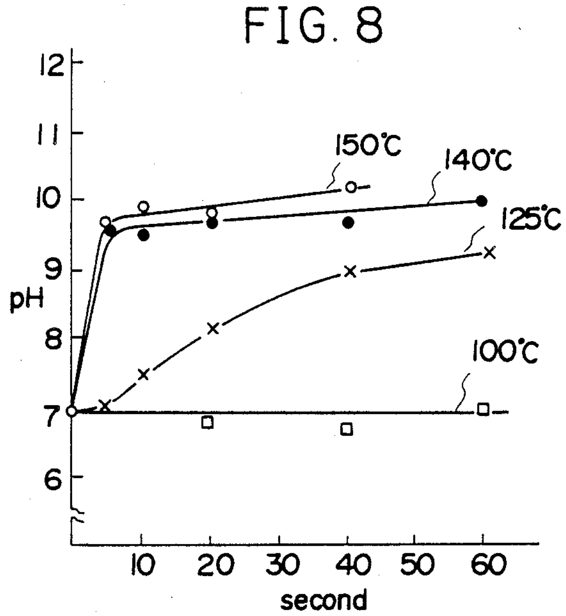

The base precursor of the present invention is in the form of a salt of an organic base with a carboxylic acid. The organic base has two to four guanidine moieties in its molecular structure. The guanidine moiety corresponding to an atomic group formed by removing one or two hydrogen atoms from a compound (guanidine or a guanidine derivative) having the following formula (I):

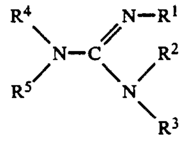
(I)

In the formula (I), each of $R^1$, $R^2$, $R^3$, $R^4$ and $R^5$ independently is a monovalent group such as hydrogen, an alkyl group, an alkenyl group, an alkynyl group, a cycloalkyl group, an aralkyl group, an aryl group and a heterocyclic group. Each of the monovalent groups may have one or more substituent groups. Each of the alkyl group, alkenyl group, alkynyl group, cycloalkyl group, aralkyl group, aryl group and heterocyclic group preferably has 1 to 6 carbon atoms (including carbon atoms contained in substituent groups). Hydrogen, an alkyl group, a cycloalkyl group, an aralkyl group and an aryl group are preferred. Hydrogen and an alkyl group are more preferred. Hydrogen is most preferred. An example of the cycloalkyl group is cyclohexyl. An example of the aralkyl group is benzyl. An example of the aryl group is phenyl.

Any two of $R^1$, $R^2$, $R^3$, $R^4$ and $R^5$ may be combined together to form a five-membered or six-membered nitrogen-containing heterocyclic ring. The heterocyclic ring preferably consists of nitrogen and carbon atoms. In other words, the five or six members of the ring preferably are only nitrogen and carbon atoms.

It is particularly preferred that the compound having the formula (I) is guanidine (having no substituent group).

In the present invention, the organic base of the base precursor is a diacidic to tetraacidic base which is composed of two to four guanidine moieties corresponding to an atomic group formed by removing one or two hydrogen atoms from the above-mentioned compound having the formula (I) and at least one linking group for the guanidine moieties.

The linking group is a residue of a hydrocarbon or a heterocyclic ring. The hydrocarbon may be a linear aliphatic, alicyclic or aromatic compound. Examples of the heterocyclic ring include pyridine and triazine. The linking group may have one or more substituent groups. Examples of the substituent group include an alkyl group (preferably having 1 to 6 carbon atoms), an alkoxy group (preferably having 1 to 6 carbon atoms), a halogen atom and hydroxyl. The linking group preferably has 1 to 10 carbon atoms (including carbon atoms contained in substituent groups), more preferably has 1 to 8 carbon atoms, and most preferably has 1 to 6 carbon atoms.

Further, the organic base is such a hydrophilic compound that the number of total carbon atoms contained in the organic base is not more than six times the number of the guanidine moieties. The number of total carbon atoms contained in the organic base is preferably not more than five times the number of the guanidine moieties, and more preferably not more than four times the number of the guanidine moieties.

The guanidine moiety preferably is a monovalent substituent group of a hydrocarbon or heterocyclic ring, as shown in the formula (II) given below. In other words, it is preferred that the guanidine moiety corresponds to an atomic group formed by removing one hydrogen atom from an guanidine having the formula (I). However, the guanidine moiety may correspond to an atomic group formed by removing two hydrogen atoms from an guanidine having the formula (I). In this case, the organic base may be in the form of a nitro-containing heterocyclic ring (e.g., a pyperazine ring).

In the base precursor of the present invention, the diacidic to tetraacidic base preferably has the following formula (II).

$$R^6(-B)_n \quad (II).$$

In the formula (II), $R^6$ is an n-valent residue of a hydrocarbon or heterocyclic ring, each of which may have one or more substituent groups. The "n" is an integer of 2 to 4. The "n" preferably is 2 or 4, and more preferably is 2. When the "n" is 2, it is preferred that the divalent residue of the hydrocarbon, which may constitute $R^6$, is an alkylene group (more preferably having 1 to 6 carbon atoms) or an arylene group (more preferably, phenylene). An example of the residue of the heterocyclic ring, which may constitute $R^6$, is a residue derived from pyridine ring.

The organic base preferably has a symmetrical chemical structure. It is particularly preferred that the diacidic to tetraacidic base having the formula (II) is symmetrical. In the present specification, the term "symmetrical organic base" means that all of the groups represented by "B" are equivalent in the molecular structure of the organic base. In concrete expression, it means that no isomer is formed, even if the groups represented by "B" are replaced by different groups.

In the formula (II), the group represented by "B" is a monovalent group corresponding to an atomic group formed by removing one hydrogen atom from an guanidine having the formula (I).

Examples of the organic base which can be used in the base precursor of the present invention are given below.

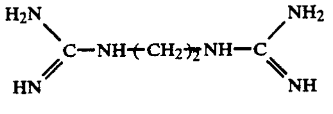
(B-1)

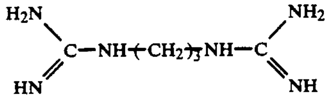
(B-2)

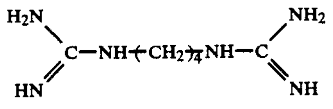
(B-3)

-continued

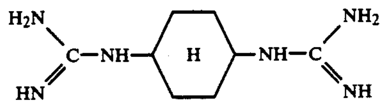
(B-4)

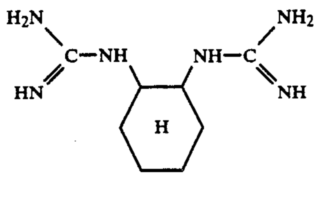
(B-5)

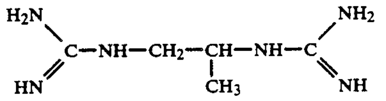
(B-6)

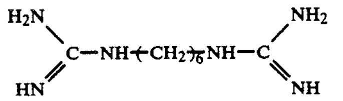
(B-7)

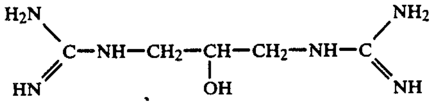
(B-8)

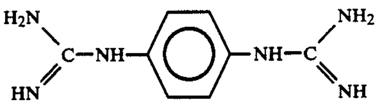
(B-9)

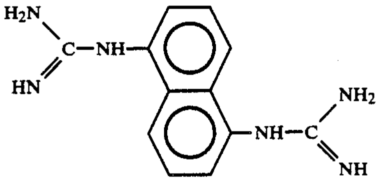
(B-10)

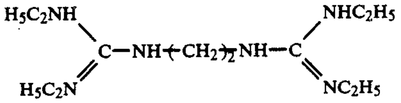
(B-11)

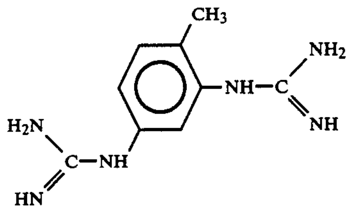
(B-12)

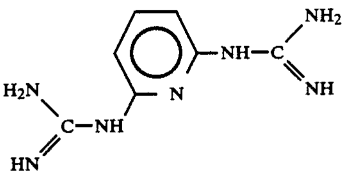
(B-13)

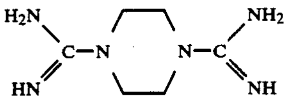
(B-14)

-continued

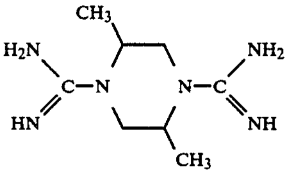

(B-15)

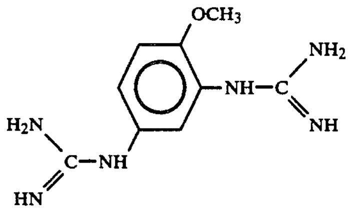

(B-16)

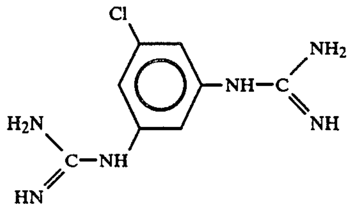

(B-17)

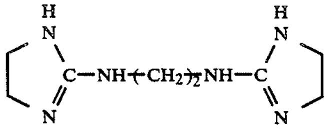

(B-18)

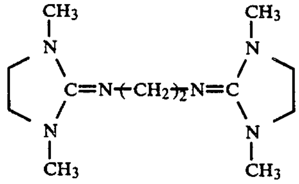

(B-19)

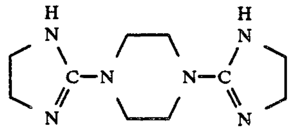

(B-20)

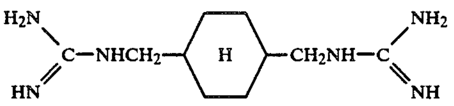

(B-21)

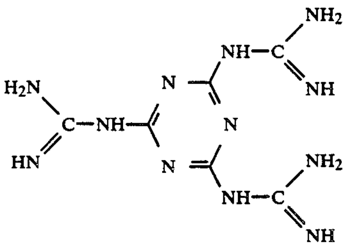

(B-22)

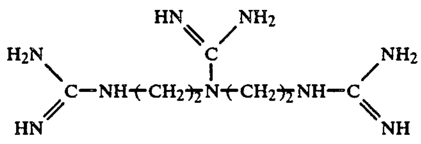

(B-23)

-continued

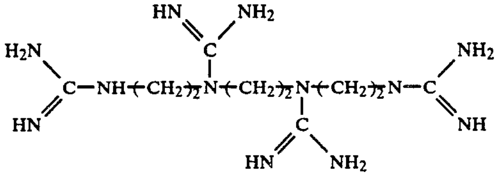

(B-24)

The carboxylic acid of the base precursor of the present invention should have such a property that the carboxyl group undergoes decarboxylation under certain conditions. However, carboxyl group generally has the above-described property so that various kinds of carboxylic acids can be used in the base precursor of the present invention.

In the case that the base precursor of the present invention is used for a heat developable recording material, it is preferred that the carboxyl group undergoes decarboxylation at an elevated temperature. The heating temperature required to decarboxylate the carboxyl group preferably is in the range of 80° to 250° C., and more preferably is in the range of 110° to 200° C.

Examples of the carboxylic acids having the above-mentioned property include trichloroacetic acid, propiolic acid and sulfonylacetic acid, which are described in the above-mentioned publications. It is preferred that the carboxylic acid has a a functional group accelerating decarboxylation such as an aryl group or an arylene group, as mentioned above. The carboxylic acid preferably is a sulfonylacetic acid having the following formula (III-1) or a propiolic acid having the following formula (III-2).

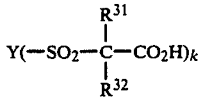

(III-1)

In the formula (III-1), each of $R^{31}$ and $R^{32}$ is a monovalent group such as hydrogen, an alkyl group, an alkenyl group, a cycloalkyl group, an aralkyl group, an aryl group and a heterocyclic group. Each of the monovalent groups may have one or more substituent groups. Among them, hydrogen, an alkyl group and an aryl group are preferred, and hydrogen is particularly preferred. Each of the alkyl group, the alkenyl group and the alkynyl group preferably has 1 to 8 carbon atoms.

In the formula (III-1), "k" is 1 or 2. When "k" is 1, Y is a monovalent group such as an alkyl group, a cycloalkyl group, an alkenyl group, an alkynyl group, an aralkyl group, an aryl group and a heterocyclic group. Among them, an aryl group and a heterocyclic group are preferred, and an aryl group is particularly preferred. Each of the monovalent groups may have one or more substituent groups. Examples of the substituent group of the aryl group include a halogen atom, an alkyl group, an alkoxyl group, an alkylsulfonyl group, an arylsulfonyl group, an acylamino group, carbamoyl and sulfamoyl.

When "k" is 2, Y is a divalent group such as an alkylene group, an arylene group and a heterocyclic group. Each of the divalent groups may have one or more substituent groups. Among them, an arylene group and a heterocyclic group are preferred, and an arylene group is particularly preferred. Examples of the substituent groups of the arylene group are the same as those of the aryl group mentioned above.

$$Z(-C\equiv C-CO_2H)_m \quad \text{(III-2).}$$

In the formula (III-2), "m" is 1 or 2. When "m" is 1, Z is a monovalent group such as hydrogen, an alkyl group, a cycloalkyl group, an alkenyl group, an alkynyl group, an aralkyl, an aryl group, a heterocyclic group and carboxyl. Each of the monovalent groups may have one or more substituent groups. Among them, an aryl group is particularly preferred.

When "m" is 2, Z is a divalent group such as an alkylene group, an arylene group and a heterocyclic group. Each of the divalent groups may have one or more substituent groups. Among them, an arylene group is particularly preferred.

Examples of the carboxylic acid are given below.

(A-1)

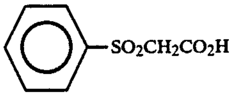

(A-2)

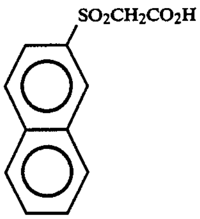

(A-3)

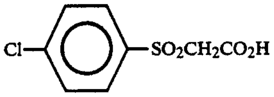

(A-4)

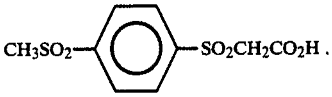

(A-5)

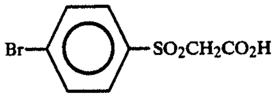

(A-6)

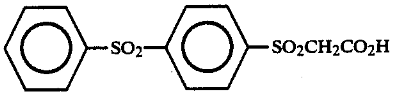

(A-7)

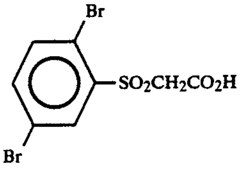

(A-8)

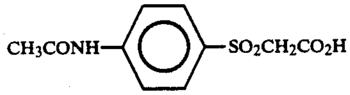

-continued (A-9)

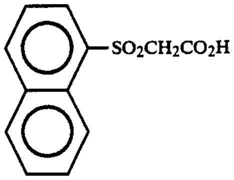

(A-10)

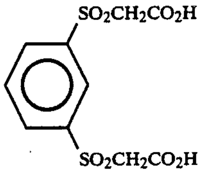

(A-11)

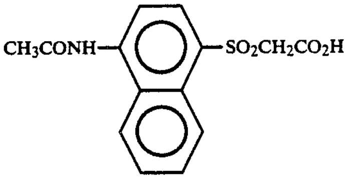

(A-12)

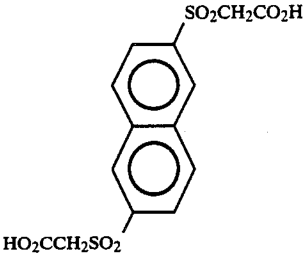

(A-13)

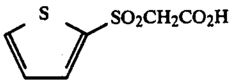

(A-14)

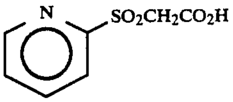

(A-15)

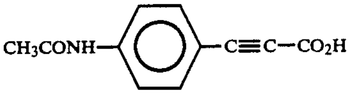

(A-16)

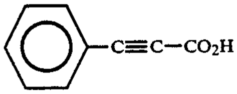

(A-17)

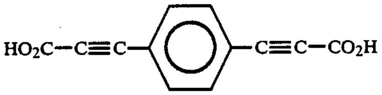

(A-18)

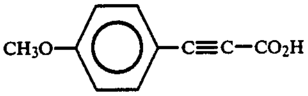

(A-19)

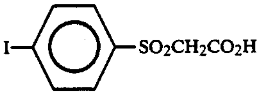

-continued (A-20)

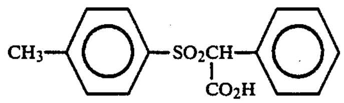

(A-21)

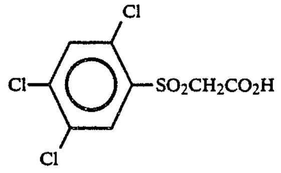

-continued (A-22)

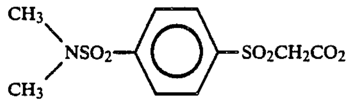

The base precursor of the present invention is in the form a salt composed of the above-mentioned carboxylic acid and organic base. There is no specific limitation with respect to a combination of the carboxylic acid and the organic base. However, it is desirable that the salt of the carboxylic acid and the organic base has a melting point of 50° to 200° C., more preferably 80° to 120° C.

Concrete examples of the base precursor of the present invention are described below. However, the present invention is not limited to the following examples.

(1)

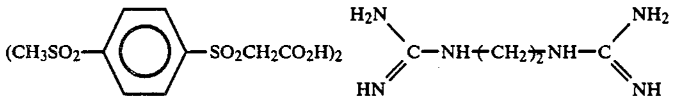

(2)

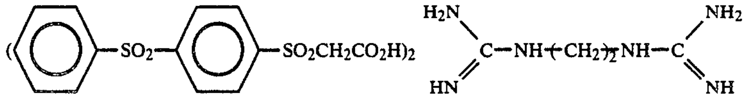

(3)

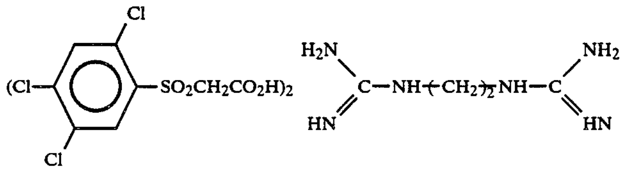

(4)

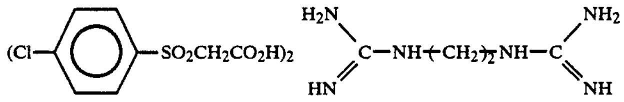

(5)

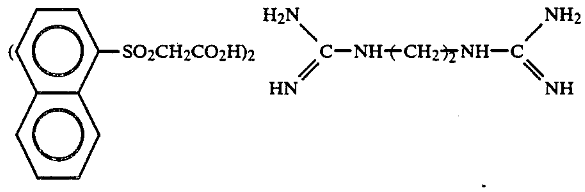

(6)

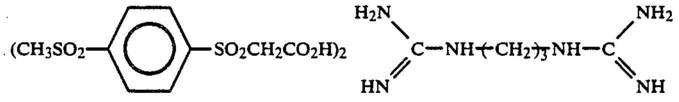

(7)

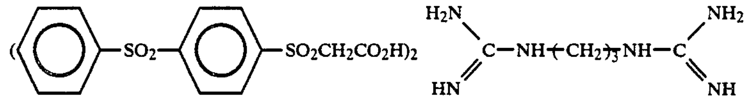

(8)

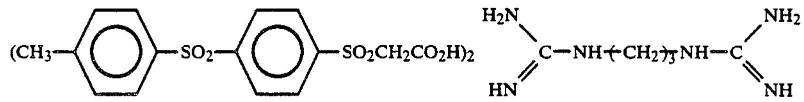

(9)

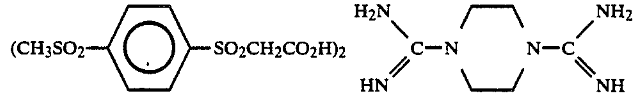

-continued
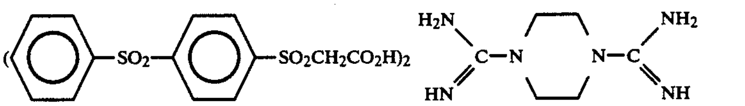
(10)
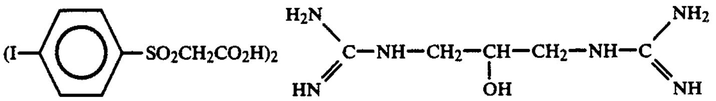
(11)
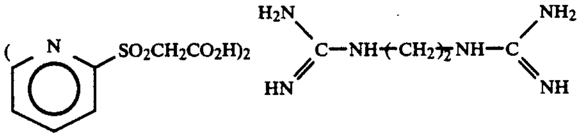
(12)
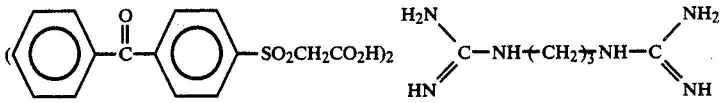
(13)
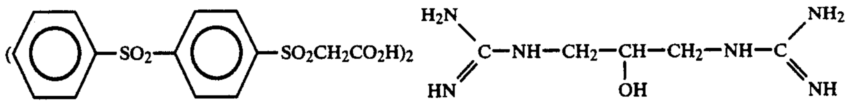
(14)
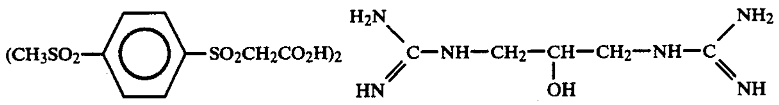
(15)
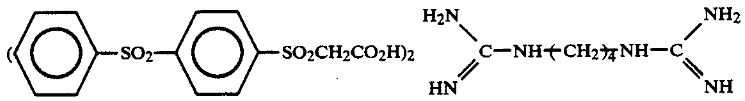
(16)
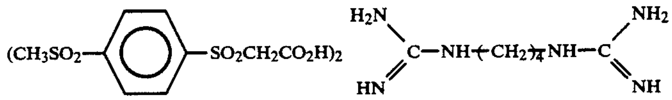
(17)
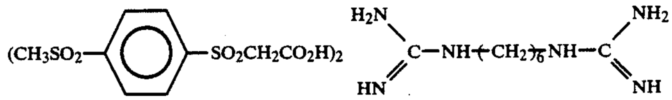
(18)
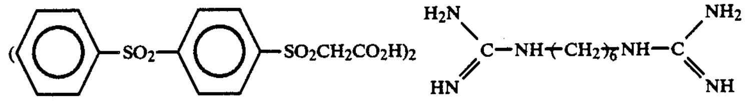
(19)
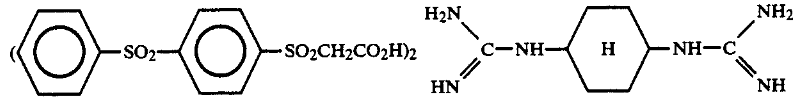
(20)
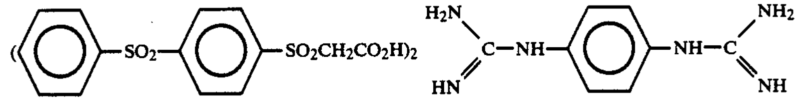
(21)
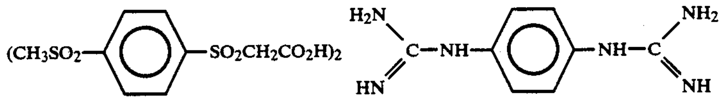
(22)

-continued
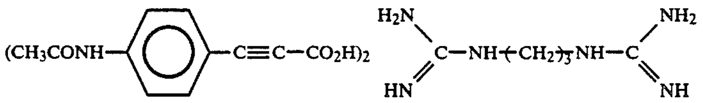
(23)
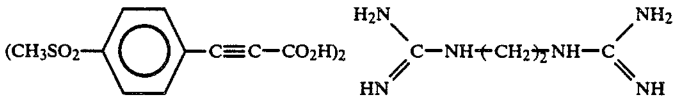
(24)
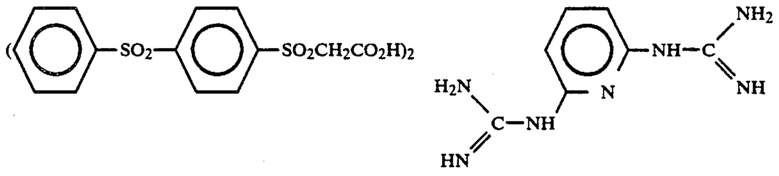
(25)
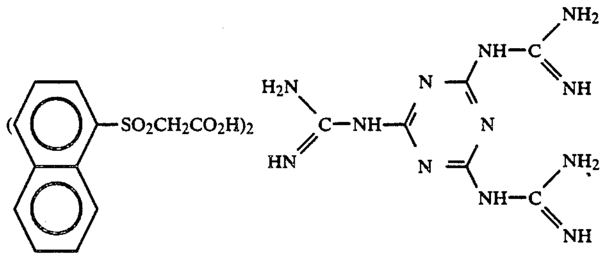
(26)
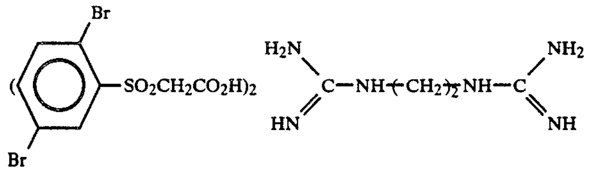
(27)
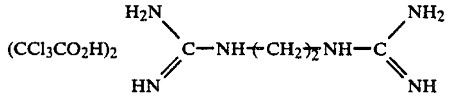
(28)
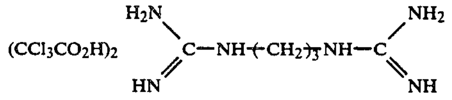
(29)
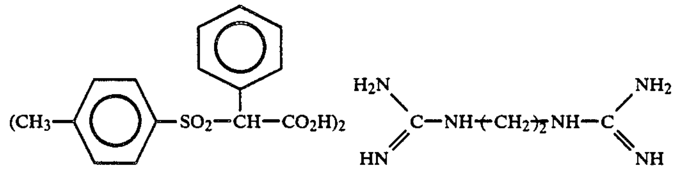
(30)
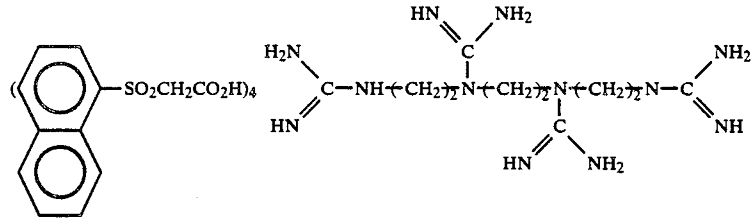
(31)

-continued
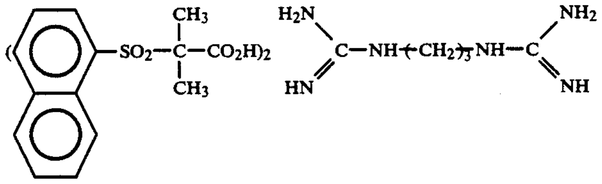
(32)
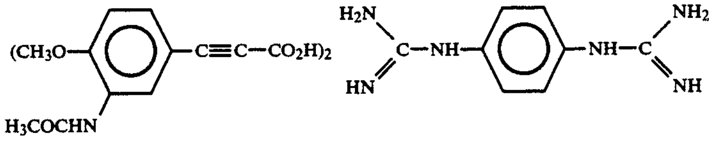
(33)
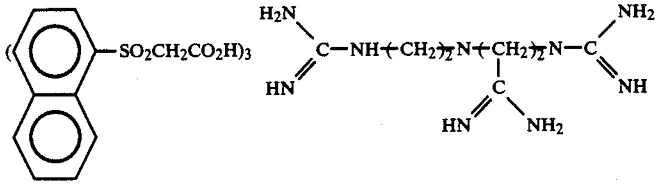
(34)
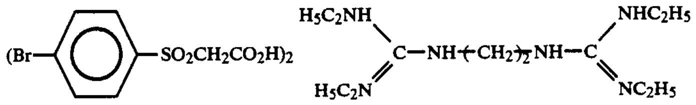
(35)
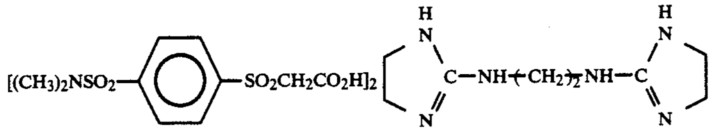
(36)
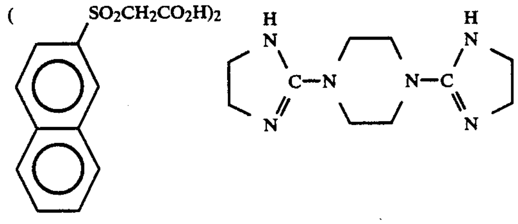
(37)
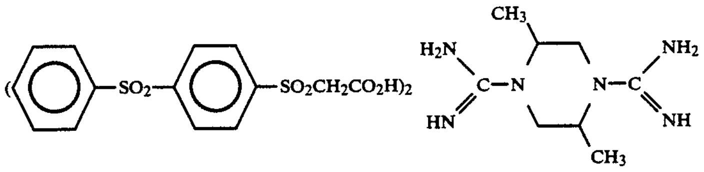
(38)
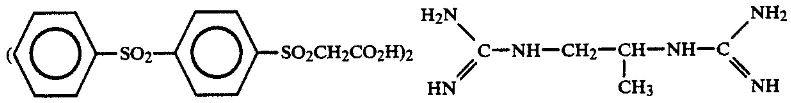
(39)
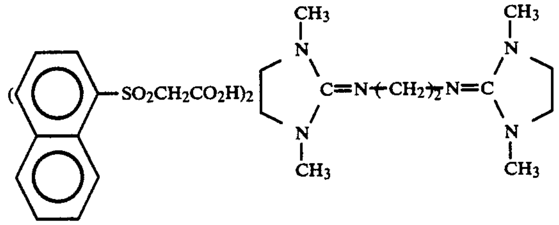
(40)

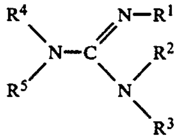

(I)

The guanidine derivatives can be synthesized by referring to the literature of "Methoden der Organischen Chemie (Houben-Weyl), 4th edition, vol. 8 (1952), pp. 18–195 and vol. E4 (1983), pp. 608–624. The guanidine derivative is synthesized according to one of the following reaction formulas (a) to (e):

(a) Reaction of a cyanamide with an amine;

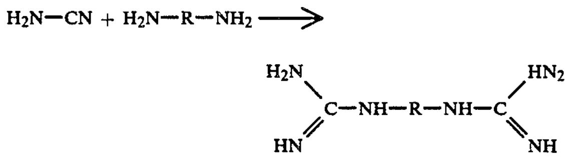

(b) Reaction of a carbodiimido with an amine;

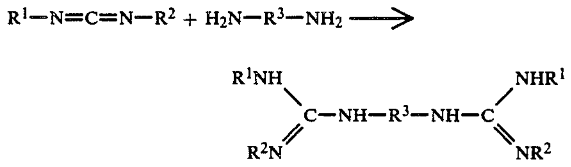

(c) Reaction of an isothiourea with an amine;

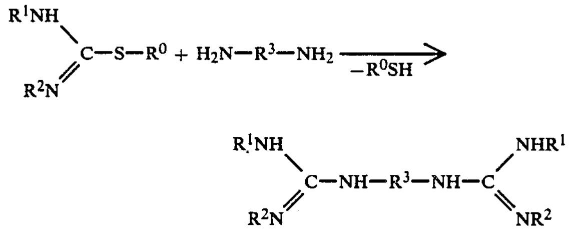

(d) Reaction of a thiourea with an amine;

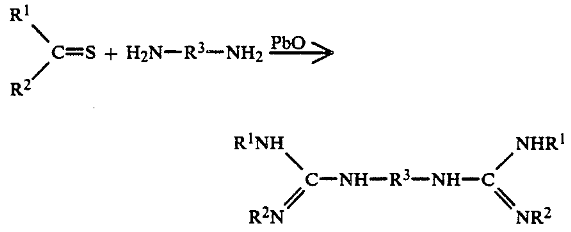

(e) Reaction of guanidine with an amine;

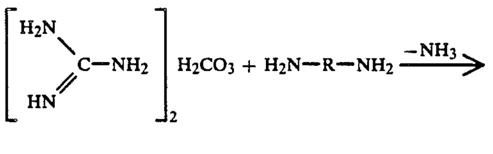

-continued

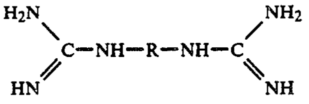

The synthesized guanidine derivative itself usually is in the form of a viscous liquid. The guanidine derivative is isolated as carbonate by reacting it with gaseous carbon dioxide.

The melting points or decomposition points of the guanidine derivatives are listed below.

| Guanidine Derivative | Decomposition Point |
|---|---|
| 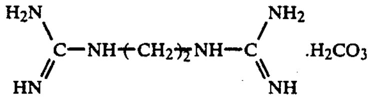 | 178–180° C. |
| 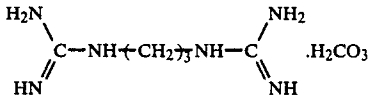 | 202–204° C. |
| 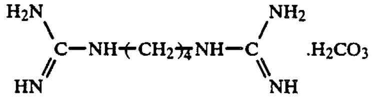 | 195–199° C. |
| 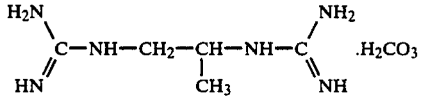 | 100–105° C. |
| 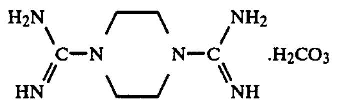 | 198–200° C. |
| | Melting Point |
| 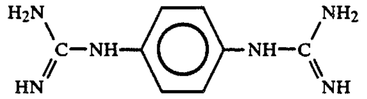 | 208–210° C. |
| 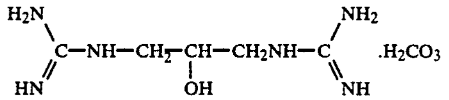 | 155–166° C. |

The acid moiety (carboxylic acid) of the base precursor can be synthesized by referring to Japanese Patent Provisional Publications Nos. 60(1985)-237443, 61(1986)-32844 and 61(1986)-84640.

Synthesis Example of the typical base precursor is described below.

SYNTHESIS EXAMPLE

Synthesis of base precursor (7)

In 4 l of methanol was dissolved 4-phenylsulfonylphenylsulfonylacetic acid upon heating. To the solution was portionwise added 132 g of 1,3-diguanidinopropane carbonate at 50° C. The obtained solution was cooled, and crystals were recovered by filtration. The yeild was 478 g (95% of theoretical value), m.p. 138°–143° C. (dec).

The other base precursors can be synthesized in a similar manner as in the Synthesis Example.

The melting points (or decomposition points) of the typical base precursors are set forth in the following Table.

In the following Table, vague melting points are designated in parentheses. The value in the parenthesis is a temperature at which both of an emission of absorption of heat and a change of weight are observed using a differential thermogravimetric analysis apparatus (produced by Seiko Instruments & Electronics Ltd.).

| Base Precursor | Melting Points |
|---|---|
| Base precursor (1) | (144° C.) |
| Base precursor (2) | 128–135° C. (dec) |
| Base precursor (5) | 110–119° C. (dec) |
| Base precursor (6) | (138° C.) |
| Base precursor (7) | 138–143° C. (dec) |
| Base precursor (9) | (186° C.) |
| Base precursor (15) | (116° C.) |
| Base precursor (16) | 155–160° C. (dec) |
| Base precursor (17) | (150° C.) |
| Base precursor (39) | 95–102° C. (dec) |

Use of the base precursor of the present invention will be described hereinbelow.

The base precursor of the present invention is advantageously used in process for formation of a base comprising a step of heating a base precursor. The base precursor is heated preferably at a temperature of 80° to 250° C., and more preferably at a temperature of 110° to 200° C. Further, the base precursor is preferably heated in the presence of a polymer (more preferably hydrophilic polymer). The polymer is preferably used in an amount of 0.5 to 400 weight %, more preferably used in an amount of 1 to 200 weight %, based on the amount of the base precursor.

The base precursor of the present invention can be effectively used in various chemical reaction systems requiring base components, such as anionic-polymerizable adhesives, coating agents, sealing and caulking agents, as well as the aforementioned recording materials, such as silver salt photographic materials, diazotype photographic materials.

The base formed from the base precursor of the present invention can be used as a basic catalyst for the polymerization reaction of anionic-polymerizable monomers. There is no specific limitation with respect to the anionic polymerization, and the base precursor of the present invention can be widely used in the various products, such as adhesives, coating agents, sealing agents, caulking agents.

When the base precursor of the present invention is used in the above-mentioned products, a base can be formed by heating the base precursor for the use of the product. Accordingly, these products can be made neutral, safe and stable by using the base precursor of the present invention.

In the method using the diazo type photographic material, a coupling reaction between a coupler and the remaining diazonium salt in the unexposed part is carried out under alkaline conditions to form an azo dye, as shown in the following formula:

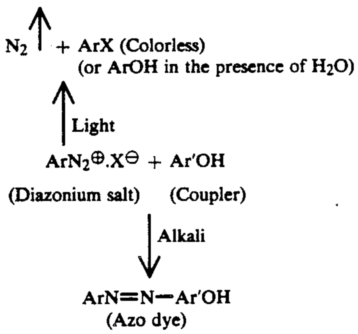

When the base precursor of the present invention is used for the above diazo type photographic method, for example, employing a dry process, the base precursor and a diazonium salt are added to a diazotype photosensitive paper in such a manner that the diazonium salt and the base precursor are isolated from each other (e.g., by the solid dispersion of the base precursor). After the photosensitive paper is imagewise exposed, an azo dye image can be obtained by heat development. In conventional diazo type photographic methods employing a heat development, base precursors such as ammonium carbonate, hexamethylenetetramine are used. In the conventional methods, the developing time is relatively long and the light-sensitive paper has a problem with respect to the stability. Where the base precursor of the present invention is used in the methods, the image can be rapidly formed and the photosensitive paper is improved in the stability.

In a conventional silver salt photographic process, the development (i.e., an oxidation-reduction reaction between silver halide and a developing agent) is carried out under an alkaline condition. Where the base precursor of the present invention is contained in the photographic material, the development can be carried out only by heating after exposure. In the photographic material, it is preferred that the base precursor is isolated from other components in the photographic material by emulsifying, dispersing or encapsulating the base precursor. It is more preferred that the base precursor is dispersed in the form of fine solid particles. The base precursor of the present invention has another advantage in that it can be effectively isolated from other components in the photosensitive material.

Further, the base precursor of the present invention can be advantageously used in a light-sensitive material which comprises a support and a light-sensitive layer containing silver halide, a reducing agent and a polymerizable compound. This light-sensitive material can be used in an image forming method in which a latent image of silver halide is formed, and then the polymerizable compound is polymerized to form the corresponding image.

Examples of said image forming methods are described in Japanese Patent Publication Nos. 45(1970)-11149 (corresponding to U.S. Pat. No. 3,697,275), 47(1972)-20741 (corresponding to U.S. Pat. No. 3,687,667) and 49(1974)-10697, and Japanese Patent Provisional Publication Nos. 57(1982)-138632, 57(1982)-142638, 57(1982)-176033, 57(1982)-211146 (corresponding to U.S. Pat. No. 4,557,997), 58(1983)-107529 (corresponding to U.S. Pat. No. 4,560,637), 58(1983)-121031 (corresponding to U.S. Pat.

No. 4,547,450) and 58(1983)-169143. In these image forming methods, when the exposed silver halide is developed using a developing solution, the polymerizable compound is induced to polymerize in the presence of a reducing agent (which is oxidized) to form a polymer image. Thus, these methods need a wet development process employing a developing solution. Therefore the process takes a relatively long time for the operation.

An improved image forming method employing a dry process is described in Japanese Patent Provisional Publications Nos. 61(1986)-69062 and 61(1986)-73145 (the contents of both publications are described in U.S. Pat. No. 4,629,676 and European Patent Provisional Publication No. 0174634A2). In this image forming method, a recording material (i.e., light-sensitive material) comprising a light-sensitive layer containing a light-sensitive silver salt (i.e., silver halide), a reducing agent, a cross-linkable compound (i.e., polymerizable compound) and a binder provided on a support is imagewise exposed to form a latent image, and then the material is heated to polymerize within the area where the latent image of the silver halide has been formed.

The above-mentioned image forming methods are based on the principle in which the polymerizable compound is polymerized within the area where a latent image of the silver halide has been formed.

Japanese Patent Provisional Publication No. 61(1986) -260241 describes another image forming method in which the polymerizable compound within the area where a latent image of the silver halide has not been formed is polymerized. In this method, when the material is heated, the reducing agent functions as polymerization inhibitor within the area where a latent image of the silver halide has been formed, and the polymerizable compound within the other area is polymerized.

The polymerization reaction in the above-mentioned image forming method smoothly proceeds under alkaline conditions. Therefore, the light-sensitive material preferably contains a base or base precursor which is arranged in the light-sensitive layer, the support or an optionally attached layer (usually in the light-sensitive layer). Examples of the base and base precursor are described in Japanese Patent Provisional Publications No. 61(1986)-69062, No. 61(1986)-73145 and 62(1987)-264041. Where a base or base precursor is contained in the light-sensitive layer prior to a heat development process, the light-sensitive material tends to be lower in sensitivity and and sharpness of the obtained image (especially in the case that a base is used). Further, the base precursors described in the above Publications are incomplete with respect to the stability in the preservation or the rate of the decomposition (i.e., releasing a base) in the heat development process.

According to the present invention, the light-sensitive material contains the above-mentioned excellent base precursor. Therefore, the light-sensitive material of the present invention can give a clear image, even if the material has been preserved for a long term or under severe conditions.

The base precursor can be arranged in the light-sensitive layer, the support or an optionally attached layer. In the light-sensitive material of the present invention, the base precursor is preferably arranged in the light-sensitive layer.

The base precursor is more preferably in the form of a dispersion of solid particles which are arranged in the light-sensitive layer. In the case that the silver halide, reducing agent and polymerizable compound are contained in microcapsules which are dispersed in the light-sensitive layer, the base precursor is preferably arranged outside of the microcapsules in the light-sensitive layer.

The base precursor is preferably contained in the light-sensitive material in an amount of 0.01 to 40 weight % based on the amount of the light-sensitive layer. Two or more base precursors can be used in the combination.

The silver halide, reducing agent, polymerizable compound and support which constitute the light-sensitive material of the invention are described below. Thus composed material is referred hereinafter to as "light-sensitive material".

There is no specific limitation with respect to silver halide contained in the light-sensitive layer of the light-sensitive material. Examples of the silver halides include silver chloride, silver bromide, silver iodide, silver chlorobromide, silver chloroiodide, silver iodobromide, and silver chloroiodobromide in the form of grains.

The halogen composition of individual grains may be homogeneous or heterogeneous. The heterogeneous grains having a multilayered structure in which the halogen composition varies from the core to the outer shell (see Japanese Patent Provisional Publication Nos. 57(1982)-154232, 58(1983)-108533, 59(1984)-48755 and 59(1984)-52237, U.S. Pat. No. 4,433,048, and European Pat. No. 100,984) can be employed. A silver halide grain having a core/shell structure in which the silver iodide content in the shell is higher than that in the core can be also employed.

There is no specific limitation on the crystal habit of silver halide grains. For example, a tubular grain having an aspect ratio of not less than 3 can be used.

The silver halide grains preferably have such a relatively low tendency to be fogged that the amount of developed silver is not more than 5 weight % based on the total amount of silver when the unexposed silver halide grains are developed in 1 l of an aqueous developing solution containing 1.0 g of metol, 15.0 g of sodium sulfite, 4.0 g of hydroquinone, 26.7 g of sodium carbonate monohydrate and 0.7 g of potassium bromide.

Two or more kinds of silver halide grains which differ in halogen composition, crystal habit, grain size, and/or other features from each other can be used in combination.

There is no specific limitation on grain size distribution of silver halide grains. For example, the silver halide grains having such a grain size distribution that the coefficient of the variation is not more than 20% can be employed.

The silver halide grains ordinarily have a mean size of 0.001 to 5 $\mu m$, more preferably 0.001 to 2 $\mu m$.

The total silver content (including silver halide and an organic silver salt which is one of optional components) in the light-sensitive layer preferably is in the range of from 0.1 $mg/m^2$ to 10 $g/m^2$. The silver content of the silver halide in the light-sensitive layer preferably is not more than 0.1 $g/m^2$, more preferably in the range of from 1 mg to 90 $mg/m^2$.

The reducing agent employed in the light-sensitive material has a function of reducing the silver halide and/or a function of accelerating or restraining a polymerization of the polymerizable compound. Examples of the reducing agents having these functions include various compounds, such as hydroquinones, catechols, p-aminophenols, p-phenylenediamines, 3-pyrazolidones, 3-aminopyrazoles, 4-amino-5-pyrazolones, 5-aminouracils, 4,5-dihydroxy-6-aminopyrimidines, reductones, aminoreductones, o- or p-sulfonamidophenols, o- or p-sulfonamidonaphthols, 2-sulfonamidoindanones, 4-sulfonamido-5-pyrazolones, 3-sulfonamidoindoles, sulfonamidopyrazolobenzimidazoles, sulfonamidopyrazolotriazoles, α-sulfonamidoketones, hydrazines, etc. Depending on the nature or amount of the reducing agent, the polymerizable compound within either the area where a latent image of the silver halide has been formed or the area where a latent image of the silver halide has not been formed can be polymerized. For example, when hydrazines are used as the reducing agent, the polymerizable compound within the area where the latent image has been formed is polymerized. Further, when 1-phenyl-3-pyrazolidone is used as the reducing agent, the polymerizable compound within the area where the latent image has not been formed is polymerized, .

The light-sensitive materials employing the reducing agent having these functions (including compounds referred to as developing agent, hydrazine derivative or precursor of reducing agent) are described in Japanese Patent Provisional Publication Nos. 61(1986)-183640, 61(1986)-188535 and 61(1986)-228441. These reducing agents are also described in T. James, "The Theory of the Photographic Process", 4th edition, pp. 291–334 (1977), Research Disclosure No. 17029, pp. 9–15 (June 1978), and Research Disclosure No. 17643, pp. 22–31 (Dec. 1978). The reducing agents described in the these publications can be employed in the light-sensitive material of the present invention. Thus, "the reducing agent(s)" in the present specification means to include all of the reducing agents described in the above mentioned publications and applications.

These reducing agents can be used singly or in combination. In the case that two or more reducing agents are used in combination, certain interactions between these reducing agents may be expected. One of the interactions is for acceleration of reduction of silver halide (and/or an organic silver salt) through so-called superadditivity. Other interaction is for a chain reaction in which an oxidized state of one reducing agent formed by a reduction of silver halide (and/or an organic silver salt) induces or inhibits the polymerization of the polymerizable compound via oxidation-reduction reaction with other reducing agent. Both interactions may occur simultaneously. Thus, it is difficult to determine which of the interactions has occurred in practical use.

Examples of these reducing agents include pentadecylhydroquinone, 5-t-butylcatechol, p-(N,N-diethylamino)-phenol, 1-phenyl-4-methyl-4-hydroxymethyl-3-pyrazolidone, 1-phenyl-4-methyl-4-heptacecylcarbonyloxymethyl-3-pyrazolidone, 2-phenylsulfonylamino-4-hexadecyloxy-5-t-octylphenol, 2-phenylsulfonylamino-4-t-butyl-5-hexadecyloxyphenol, 2-(N-butylcarbamoyl)-4-phenylsulfonylaminonaphtol, 2-(N-methyl-N-octadecylcarbamoyl)-4-sulfonylaminonaphthol, 1-acetyl-2-phenylhydrazine, 1-acetyl-2-(p- or o-aminophenyl)hydrazine, 1-formyl-2-(p- or o-aminophenyl)hydrazine, 1-acetyl-2-(pi or o-methoxyphenyl)-hydrazine, 1-lauroyl-2-(p- or o aminophenyl)hydrazine, 1-trityl-2-(2,6-dichloro-4-cyanophenyl)hydrazine, 1-trityl-2-phenylhydrazine, 1-phenyl-2-(2,4,6-trichlorophenyl)hydrazine, 1-{2-(2,5-di-tert-pentylphenoxy)-butyloyl}-2-(p- or o-aminophenyl)hydrazine, 1-{2-(2,5-di-t-pentylphenoxy)-butyloyl}-2-(p-or o-aminophenyl)-hydrazine pentadecylfluorocaprylate salt, 3-indazolinone, 1-(3,5-dichlorobenzoyl)-2-phenylhydrazine, 1-trityl-2-[{(2-N-butyl-N-octylsulfamoyl)-4-methanesulfonyl}phenyl]hydrazine, 1-{4-(2,5-di-tert-pentylphenoxy)butyloyl}-2-(p-or o-methoxyphenyl)hydrazine, 1-(methoxycarbonylbenzohydryl)-2-phenylhydrazine, 1-formyl-2-[4-{2-(2,4-di-tert-pentylphenoxy)-butylamide}phenyl]hydrazine, 1-acetyl-2-[4-{2-(2,4-di-tert-pentylphenoxy)butylamido}phenyl]hydrazine, 1-trityl-2-[{2,6-dichloro-4-(N,N-di-2-ethylhexyl)carbamoyl}phenyl]hydrazine, 1-(methoxycarbonylbenzohydryl)-2-(2,4-dichlorophenyl)hydrazine, 1-trityl-2-[{2-(N-ethyl-N-octylsulfamoyl)-4-methanesulfonyl}phenyl]hydrazine, 1-benzoyl-2-tritylhydrazine, 1-(4-butoxybenzoyl)-2-tritylhydrazine, 1-(2,4-dimethoxybenzoyl)-2-tritylhydrazine, 1-(4-dibutylcarbamoylbenzoyl)-2-tritylhydrazine and 1-(1-naphthoyl)-2-tritylhydrazine.

The amount of the reducing agent in the light-sensitive layer preferably ranges from 0.1 to 1,500 mole % based on the amount of silver (contained in the above-mentioned silver halide and an organic silver salt).

There is no specific limitation with respect to the polymerizable compound, except that the compound has an ethylenic unsaturated group. Any known ethylenic unsaturated polymerizable compounds including monomers, oligomers and polymers can be contained in the light-sensitive layer. In the image-forming method of the invention, a polymerizable compounds having a relatively higher boiling point (e.g., 80° C. or higher) is prebarably employed because it is hardly evaporated upon heating. In the case that the light-sensitive layer contains a color image forming substance, the polymerizable compounds are preferably cross-linkable compounds having plural polymerizable groups in the molecule, because such cross-linkable compounds favorably serve for fixing the color image forming substance in the course of polymerization hardening of the polymerizable compounds. Further, in the case that a transferred image is formed on an image-receiving material, the polymerizable compound preferably has a viscosity of not lower than 100 cP at 25° C.

Examples of compounds having an ethylenic unsaturated group include acrylic acid, salts of acrylic acid, acrylic esters, acrylamides, methacrylic acid, salts of methacrylic acid, methacrylic esters, methacrylamide, maleic anhydride, maleic esters, itaconic esters, styrene, styrene derivatives, vinyl ethers, vinyl esters, N-vinyl heterocyclic compounds, allyl ethers, allyl esters, and compounds carrying a group or groups corresponding to one or more of these compounds.

Concrete examples of the acrylic esters include n-butyl acrylate, cyclohexyl acrylate, 2-ethylhexyl acrylate, benzyl acrylate, furfuryl acrylate, ethoxyethoxy acrylate, dicyclohexyloxyethyl acrylate, nonylphenyloxyethyl acrylate, hexanediol diacrylate, butanediol diacrylate, neopentylglycol diacrylate, trimethylolpropane triacrylate, pentaerythritol tetraacrylate, dipentaerythritol pentaacrylate, diacrylate of polyoxyethylenated bisphenol A, polyacrylate of hydroxypolyether, polyester acrylate, and polyurethane acrylate.

Concrete examples of the methacrylic esters include methyl methacrylate, butyl methacrylate, ethylene glycol dimethacrylate, butanediol dimethacrylate, neopentylglycol dimethacrylate, trimethylolpropane trimethacrylate, pentaerythritol trimethacrylate, pentaerythritol tetramethacrylate, and dimethacrylate of polyoxyalkylenated bisphenol A.

The polymerizable compounds can be used singly or in combination of two or more compounds. For example, a mixture of two or more polymerizable componds can be employed. Further, compounds formed by bonding a polymerizable group such as a vinyl group or a vinylidene group to a reducing agent or a color image forming substance are also employed as the polymerizable compounds. The light-sensitive materials employing these compounds which show functions as both the reducing agent and the polymerizable compound, or of the color image forming substance and the polymerizable compound are included in embodiments of the invention.

The amount of the polymerizable compound for incorporation into the light-sensitive layer preferably ranges from 5 to $1.2 \times 10^5$ times (by weight) as much as the amount of silver halide, more preferably from 10 to $1 \times 10^4$ times as much as the silver halide.

The light-sensitive material can be prepared by arranging a light-sensitive layer containing the abovementioned components on a support. There is no limitation with respect to the support. In the case that a heat development is unilized in the use of the light-sensitive material, the support preferably is resistant to heat given in the processing stage. Examples of the material employable as the support include glass, paper, fine paper, coat paper, cast-coated paper, baryta paper, synthetic paper, metals and analogues thereof, polyester, acetyl cellulose, cellulose ester, polyvinyl acetal, polystyrene, polycarbonate, polyethylene terephthalate, and paper laminated with resin or polymer (e.g., polyethylene). In the case that a porous material, such as paper is employed as the support, the porous support preferably has such a surface characteristic that a filtered maximum waviness of not less than 4 μm is observed in not more than 20 positions among 100 positions which are determined at random on a filtered waviness curve obtained according to JIS-B-0610. A surface of a paper support preferably has a low water absorptiveness of not more than 3 $g/m^2$ which is a value measured according to Cobb test method. A surface of the paper support preferably has such a smooth surface that the smoothness value in terms of the Bekk Smoothness is not less than 300 seconds. A paper support preferably has a low shrinkage ratio of not more than 0.15% both in the machine direction and in the cross direction, wherein the shrinkage ratio is a value measured at the change of relative humidity from 75% to 60%. Further, a paper support preferably has a low air permeability of not less than 300 seconds, wherein the air permeability is a time required for 100 ml of air to pass through the paper support of an area of 645 $mm^2$ at pressure of 567 g. Furthermore, a paper support preferably has a pH value in the range of 5 to 9.

Various embodiments of the light-sensitive materials, optional components which may be contained in the light-sensitive layer, and auxiliary layers which may be optionally arranged on the light-sensitive materials are described below.

The polymerizable compound is preferably dispersed in the form of oil droplets in the light-sensitive layer. Other components in the light-sensitive layer, such as reducing agent and a color image forming substance may be also contained in the oil droplets. In the case that the silver halide is contained in the oil droplets, it is preferred that five or more silver halide grains are contained in the oil droplets.

The oil droplets of the polymerizable compound are preferably in the form of microcapsules. There is no specific limitation with respect to a process for the preparation of microcapsules, and the various known processes can be employed.

There is also no specific limitation on shell material of the microcapsules, and various known materials such as polymers which are employed in the conventional microcapsules can be employed as the shell material. Examples of the shell material include polyamide resin and/or polyester resin, polyurea resin and/or polyurethane resin, aminoaldehyde resin, gelatin, epoxy resin, a complex resin comprising polyamide resin and polyurea resin, and a complex resin comprising polyurethane resin and polyester resin.

In the case that the shell material is composed of a condensed aldehyde resin, the residual aldehyde preferably is not more than 5 mole based on 1 mole of the reducing agent.

The microcapsules which contains five or more silver halide grains are preferably more than 50% by weight based on the total amount of the microcapsules. It is preferred that at least 70 weight % (more preferably at least 90 weight %) of the silver halide grains are arranged in the shell material of the microcapsules.

Further, two or more kinds of the microcapsules differing from each other with respect to at least one of the silver halide, polymerizable compound and color image forming substance can be employed. Furthermore, three or more kinds of the microcapsules differing from each other with respect to the color image forming substance is preferably employed to form a full color image.

The mean size of the microcapsule preferably ranges from 0.5 to 50 μm, more preferably 1 to 25 μm, most preferably 3 to 20 μm. The amount of the microcapsules having a particle size of not larger than one sixth part of the average particle size preferably is not more than 1 volume % of the total amount of the microcapsules. Further, the amount of the microcapsules having a particle size of not smaller than twice as large as the average particle size is not more than 1 volume % of the total amount of the microcapsules. Furthermore, the proportion of an average thickness of the shell of the microcapsules to the average particle size preferably ranges from $0.5 \times 10^{-2}$ to $5 \times 10^{-2}$.

The mean grain size of the silver halide grains preferably is not more than the 5th part of the mean size of the microcapsules, more preferably is not more than 10th part. It is observed that when the mean size of the microcapsules is not less than 5 times as much as the mean grain size of silver halide grains, even and uniform image can be obtained.

The light-sensitive layer can further contain optional components such as color image forming substances, sensitizing dyes, organic silver salts, radical generators, various kinds of image formation accelerators, thermal polymerization inhibitors, thermal polymerization initiators, development stopping agents, flurorescent brightening agents, discoloration inhibitors, antihalation dyes or pigments, antiirradiation dyes or pigments, dyes having a property of being decolorized when it is heated or irradiated with light, matting agents, antismudging agents, plasticizers, water releasers, binders, photo polymerization initiator, solvent of the polymerizable compound and water soluble vinyl polymers.

The light-sensitive material containing the abovementioned components can give a polymer image. When the light-sensitive material further contains a color image forming substance as an optional component, the material can give a color image.

There is no specific limitation with respect to the color image forming substance, and various kinds of substances can be employed. Thus, examples of the color image forming substance include both colored substance (i.e., dyes and pigments) and non-colored or almost noncolored substance (i.e., color former or dye- or pigmentprecursor) which develops to give a color under application of external energy (e.g., heating, pressing, light irradiation, etc.) or by contact with other components (i.e., developer). The light-sensitive material using the color image forming substance is described in Japanese Patent Provisional Publication No. 61(1986)-73145 (corresponding to U.S. Pat. No. 4,629,676 and European Patent Provisional Publication No. 0174634A2).

Examples of the dyes and pigments (i.e., colored substances) employable in the invention include commercially available ones, as well as various known compounds described in the technical publications, e.g., Yuki Gosei Kagaku Kyokai (ed.), Handbook of Dyes (in Japanese, 1970) and Nippon Ganryo Gijutsu Kyokai (ed.), New Handbook of Pigments (in Japanese, 1977). These dyes and pigments can be used in the form of a solution or a dispersion.

Examples of the substances which develop to give a color by certain energy includes thermochromic compounds, piezochromic compounds, photochromic compounds and leuco compounds derived from triarylmethane dyes, quinone dyes, indigoid dyes, azine dyes, etc. These compounds are capable of developing a color by heating, application of pressure, light-irradiation or air-oxidation.

Examples of the substances which develop to give a color in contact with other components include various compounds capable of developing a color through some reaction between two or more components, such as acid-base reaction, oxidation-reduction reaction, coupling reaction, chelating reaction, and the like. Examples of such color formation systems are described in Hiroyuki Moriga, "Introduction of Chemistry of Speciality Paper" (in Japanese, 1975) pp. 29–58 (pressure-sensitive copying paper), pp. 87–95 (azo-graphy), pp. 118–120 (heat-sensitive color formation by a chemical change) or in MSS. of the seminer promoted by the Society of Kinki Chemical Industry, "The Newest Chemistry of Coloring Matter - Attractive Application and New Development as a Functional Coloring Matter", pp. 26–32 (June, 19, 1980). Examples of the color formation systems specifically include a color formation system used in pressure-sensitive papers, etc., comprising a color former having a partial structure of lactone, lactam, spiropyran, etc., and an acidic substance (developer), e.g., acid clay, phenol, etc.; a system utilizing azo-coupling reaction between an aromatic a diazonium salt, diazotate or diazosulfonate and naphthol, aniline, active methylene, etc.; a system utilizing a chelating reaction, such as a reaction between hexamethylenetetramine and a ferric ion and gallic acid, or a reaction between a phenolphthalein-complexon and an alkaline earth metal ion; a system utilizing oxidation-reduction reaction, such as a reaction between ferric stearate and pyrogallol, or a reaction between silver behenate and 4-methoxy-1-naphthol, etc.

The color image forming substance in the light-sensitive material is preferably used in an amount of from 0.5 to 20 parts by weight, and more preferably from 2 to 7 parts by weight, per 100 parts by weight of the polymerizable compound. In the case that the developer is used, it is preferably used in an amount of from about 0.3 to about 80 parts by weight per one part by weight of the color former.

In the case that the color image forming substance comprises two components (e.g., color former and a developer), one component and the polymerizable compound is contained in the microcapsule, and the other component is arranged outside of the microcapsule in the light-sensitive layer, a color image can be formed on the light-sensitive layer.

There is no specific limitation with respect to the sensitizing dyes, and known sensitizing dyes used in the conventional art of photography may be employed in the light-sensitive material. Examples of the sensitizing dyes include methine dyes, cyanine dyes, merocyanine dyes, complex cyanine dyes, complex merocyanine dyes, holopolar cyanine dyes, hemicyanine dyes, styryl dyes, and hemioxonol dyes. These sensitizing dyes can be used singly or in combination. Combinations of sensitizing dyes are often used for the purpose of supersensitization. In addition to the sensitizing dyes, a substance which does not per se exhibit spectral sensitization effect or does not substantially absorb visible light but shows supersensitizing activity can be used. The amount of the sensitizing dye to be added generally ranges from about $10^{-8}$ to about $10^{-2}$ mol per 1 mol of silver halide. The sensitizing dye is preferably added during the stage of the preparation of the silver halide emulsion (simultaneously with or after the grain formation).

In the heat-development process, an organic silver salt is preferably contained in the light-sensitive material. It can be assumed that the organic silver salt takes part in a redox reaction using a silver halide latent image as a catalyst when heated to a temperature of 80° C. or higher. In such case, the silver halide and the organic silver salt preferably are located in contact with each other or close together. Examples of organic compounds employable for forming such organic silver salt include aliphatic or aromatic carboxylic acids, thiocarbonyl group-containing compounds having a mercapto group or an α-hydrogen atom, imino group-containing compounds, and the like. Among them, benzotriazoles are most preferable. The organic silver salt is preferably used in an amount of from 0.01 to 10 mol., and preferably from 0.01 to 1 mol., per 1 mol. of the light-sensitive silver halide. Instead of the organic silver salt, an organic compound (e.g., benzotriazole) which can form an organic silver salt in combination with an inoganic silver salt can be added to the light-sensitive layer to obtain the same effect.

Examples of the radical generators include triazene-silver, silver diazotate and an azo compound.

Various image formation accelerators are employable in the light-sensitive material. The image formation accelerators have a function to accelerate the oxidation-reduction reaction between a silver halide (and/or an organic silver salt) and a reducing agent, a function to accelerate emigration of an image forming substance from a light-sensitive layer to an image-receiving material or an image-receiving layer, or a similar function. The image formation accelerators can be classified into oils, surface active agents, compounds functioning as an antifogging agent and/or a development accelerator, antioxidants and the like. These groups, however, generally have certain combined functions, i.e., two or more of the above-mentioned effects. Thus, the above classification is for the sake of convenience, and one compound often has a plurality of functions combined.

Various examples of these image formation accelerators are shown below.

Examples of the oils employable in the invention include high-boiling organic solvents which are used as solvents in emulsifying and dispersing hydrophobic compounds.

Examples of the surface active agents employable in the invention include pyridinium salts, ammonium salts and phosphonium salts as described in Japanese Patent Provisional Publication No. 59(1984)-74547; polyalkylene oxides as described in Japanese Patent Provisional Publication No. 59(1984)-57231.

The compounds functioning as an antifogging agent and/or a development accelerator are used to give a clear image having a high maximum density and a low minimum density (an image having high contrast). Examples of the compounds include a 5- or 6-membered nitrogen containing heterocyclic compound (including a cyclic amide compound), a thiourea derivative, a thioether compound, a polyethylene glycol derivative, a thiol derivative, an acetylene compound, a sulfonamide derivative and a quarternary ammonium salt.

The hot-melt solvents preferably are compounds which may be used as solvent of the reducing agent or those which have high dielectric constant and can accelerate physical development of silver salts. Examples of the hot-melt solvents include polyethylene glycols, derivatives of polyethylene oxides (e.g., oleate ester), beeswax, monostearin and high dielectric constant compounds having -$SO_2$- and/jor -CO-group described in U.S. Pat. No. 3,347,675; polar compounds described in U.S. Pat. No. 3,667,959; and 1,10-decanediol, methyl anisate and biphenyl suberate described in Research Disclosure pp. 26–28 (Dec. 1976). The hot-melt solvent is preferably used in an amount of from 0.5 to 50% by weight, and more preferably from 1 to 20% by weight, based on the total solid content of the light-sensitive layer.

The antioxidants can be used to eliminate the influence of the oxygen which has an effect of inhibiting polymerization in the development process. Example of the antioxidants is a compound having two or more mercapto groups.

The thermal polymerization initiators employable in the light-sensitive material preferably are compounds that are decomposed under heating to generate a polymerization initiating species, particularly a radical, and those commonly employed as initiators or radical polymerization. The thermal polymerization initiators are described in "Addition Polymerization and Ring Opening Polymerization", pp. 6–18, edited by the Editorial Committee of High Polymer Experimental Study of the High Polymer Institute, published by Kyoritsu Shuppan (1983). Examples of the thermal polymerization initiators include azo compounds, e.g., azobisisobutyronitrile, 1,1'-azobis-(1 -cyclohexanecarbonitrile), dimethyl 2,2'-azobisiso-butyrate, 2,2'-azobis(2-methylbutyronitrile), and azobisdimethylvaleronitrile; organic peroxides, e.g., benzoyl peroxide, di-tert-butyl peroxide, dicumyl peroxide, tertbutyl hydroperoxide, and cumene hydroperoxide; inorganic peroxides, e.g., hydrogen peroxide, potassium persulfate, and ammonium persulfate; and sodium p-toluenesulfinate. The thermal polymerization initiators are preferably used in an amount of from 0.1 to 120% by weight, and more preferably from 1 to 10% by weight, based on amount of the polymerizable compound. In a system in which the polymerizable compound within the area where the latent image has not been formed is polymerized, the thermal polymerization initiators are preferably incorporated into the light-sensitive layer. The light-sensitive material employing the thermal polymerization initiators is described in Japanese Patent Provisional Publication No. 61(1986)-260241.

The development stopping agents employable in the light-sensitive material are compounds that neutralize a base or react with a base to reduce the base concentration in the layer to thereby stop development, or compounds that mutually react with silver or a silver salt to suppress development. More specifically, examples of the development stopping agents include acid precursors capable of releasing acids upon heating electrophilic compounds capable of undergoing substitution reaction with a coexisting base upon heating, nitrogen-containing heterocyclic compounds, mercapto compounds, and the like. Examples of the acid precursors include oxide esters described in Japanese Patent Provisional Publication Nos. 60(1985)-108837 and 60(1985)-192939 and compounds which release acids through Lossen rearrangement described in Japanese Patent Provisional Publication No. 60(1985)-230133. Examples of the electrophilic compounds which induce substitution reaction with bases upon heating are described in Japanese Patent Provisional Publication No. 60(1985)-230134.

The dyes or pigments can be contained in the light-sensitive layer for the purpose of anti-halation or anti-irradiation. Further, white pigments can be contained in the light-sensitive layer for the purpose of anti-halation or anti-irradiation.

The dyes having a property of being decolorized when it is heated or irradiated with light can be used in the light-sensitive material as a yellow filter layer in a conventional silver salt photographic system.

The antismudging agents employable in the light-sensitive material preferably are particles which are solid at ambient temperatures. Examples of the antismudging agents include starch particles described in U.K. Pat. No. 1,232,347; polymer particles described in U.S. Pat. No. 3,625,736; microcapsule particles containing no color former described in U.K. Pat. No. 1,235,991; and cellulose particles, and inorganic particles, such as particles of talc, kaolin, bentonite, agalmatolite, zinc oxide, titanium dioxide or aluminum oxide described in U.S. Pat. No. 2,711,375. Such particles preferably have a mean size of 3 to 50 μm, more preferably 5 to 40 μm. The size of said particle is preferably larger than that of the microcapsule.

Binders employable in the light-sensitive material preferably are transparent or semi-transparent hydrophilic binders. Examples of the binders include natural substances, such as gelatin, gelatin derivatives, cellulose derivatives, starch, and gum arabic; and synthetic polymeric substances, such as water-soluble polyvinyl compounds e.g., polyvinyl alcohol, polyvinylpyrrolidone, and acrylamide polymers. In addition to the synthetic polymeric substances, vinyl compounds dispersed in the form of latex, which are particularly effective to increase dimensional stability of photographic materials, can be also used. These binders can be used singly or in combination. The light-sensitive material employing a binder is described in Japanese Patent Provisional Publication No. 61(1986)-69062 (corresponding to U.S. Pat. No. 4,629,676 and European Patent Provisional Publication No. 0174634A2).

A photo polymerization initiator can be contained in the light-sensitive layer to polymerize the unpolymerized polymerizable compound after the image-formation.

In the case that the solvent of the polymerizable compound is used, the solvent is preferably contained in a microcapsule which is different from the light-sensitive microcapsule.

In the case that the water soluble vinyl polymer is is used, the polymers are preferably adsorbed on the silver halide grains.

Examples and usage of the other optional components which can be contained in the light-sensitive layer are also described in the above-mentioned publications and applications concerning the light-sensitive material, and in Research Disclosure Vol. 170, No. 17029, pp. 9–15 (June 1978). The light-sensitive layer preferably has a pH value of not more than 7.

Examples of auxiliary layers which are optionally arranged on the light-sensitive material include an image-receiving layer, a heating layer, a antistatic layer, an anticurl layer, a release layer, a cover sheet or a protective layer and an antihalation layer (colored layer).

Instead of the use of the image-receiving material, the image-receiving layer can be arranged on the light-sensitive material to produce the desired image on the image-receiving layer of the light-sensitive material. The image-receiving layer of the light-sensitive material can be constructed in the same manner as the layer of the image-receiving material. The details of the image-receiving layer will be described later.

Examples and usage of the other auxiliary layers are also described in the above-mentioned publications and applications concerning the light-sensitive material.

The light-sensitive material can be prepared, for instance, by the following process.

The light-sensitive material is usually prepared by dissolving, emulsifying or dispersing each of the components of the light-sensitive layer in an adequate medium to obtain coating solution, and then coating the obtained coating solution on a support.

The coating solution can be prepared by mixing liquid compositions each containing a component of the light-sensitive layer. Liquid composition containing two or more components may be also used in the preparation of the coating solution. Some components of the light-sensitive layer can be directly added to the coating solution or the liquid composition. Further, a secondary composition can be prepared by emulsifying the oily (or aqueous) composition in an aqueous (or oily) medium to obtain the coating solution.

Preparations of liquid compositions and coating solutions of the components contained in the light-sensitive layer are described hereinbelow.

The silver halide is preferably prepared in the form of a silver halide emulsion. Various processes for the preparation of the silver halide emulsion are known in the conventional technology for the preparation of photographic materials.

The silver halide emulsion can be prepared by the acid process, neutral process or ammonia process. In the stage for the preparation, a soluble silver salt and a halogen salt can be reacted in accordance with the single jet process, double jet process or a combination thereof. A reverse mixing method, in which grains are formed in the presence of excess silver ions, or a controlled double jet process, in which a pAg value is maintained constant, can be also employed. In order to accelerate grain growth, the concentrations or amounts or the silver salt and halogen salt to be added or the rate of their addition can be increased as described in Japanese Patent Provisional Publication Nos. 55(1980)-142329 and 55(1980)-158124, and U.S. Pat. No. 3,650,757, etc.

The silver halide emulsion may be of a surface latent image type that forms a latent image predominantly on the surface of silver halide grains, or of an inner latent image type that forms a latent image predominantly in the interior of the grains. A direct reversal emulsion comprising an inner latent image type emulsion and a nucleating agent may be employed. The inner latent image type emulsion suitable for this purpose is described in U.S. Pat. Nos. 2,592,250 and 3,761,276, Japanese Patent Publication No. 58(1983)-3534 and Japanese Patent Provisional Publication No. 57(1982)-136641, etc. The nucleating agent that is preferably used in combination with the inner latent image type emulsion is described in U.S. Pat. Nos. 3,227,552, 4,245,037, 4,255,511, 4,266,013 and 4,276,364, and West German Patent Provisional Publication (OLS) No. 2,635,316.

In the preparation of the silver halide emulsions, hydrophilic colloids are advantageously used as protective colloids. Examples of usable hydrophilic colloids include proteins, e.g., gelatin, gelatin derivatives, gelatin grafted with other polymers, albumin, and casein; cellulose derivatives, e.g., hydroxyethyl cellulose, carboxymethyl cellulose, cellulose sulfate, etc.; saccharide derivatives, e.g., sodium alginate and starch derivatives; and a wide variety of synthetic hydrophilic polymers, such as polyvinyl alcohol, polyvinyl alcohol partial acetal, poly-N-vinylpyrrolidone, polyacrylic acid, polymethacrylic acid, polyacrylamide, polyvinylimidazole, and polyvinylpyrazole, and copolymers comprising monomers constituting these homopolymers. Among them, gelatin is most preferred. Examples of employable gelatins include not only lime-processed gelatin, but also acid-processed gelatin and enzyme-processed gelatin. Hydrolysis products or enzymatic decomposition products of gelatin can also be used.

In the formation of silver halide grains in the silver halide emulsion, ammonia, an organic thioether derivative as described in Japanese Patent Publication No. 47(1972)-11386 or sulfur-containing compound as described in Japanese Patent Provisional Publication No. 53(1978)-144319 can be used as a silver halide solvent. Further, in the grain formation or physical ripening, a cadmium salt, a zinc salt, a lead salt, a thallium salt, or the like can be introduced into the reaction system. Furthermore, for the purpose of overcoming high or low intensity reciprocity law failure, a water-soluble iridium salt, e.g., iridium (III) or (IV) chloride, or ammonium hexachloroiridate, or a water-soluble rhodium salt, e.g., rhodium chloride can be used.

After the grain formation or physical ripening, soluble salts may be removed from the resulting emulsion by a known noodle washing method or a sedimentation method. The silver halide emulsion may be used in the primitive condition, but is usually subjected to chemical sensitization. Chemical sensitization can be carried out by the sulfur sensitization, reduction sensitization or noble metal sensitization, or a combination thereof that are known for emulsions for the preparation of the conventional light-sensitive materials.

When the sensitizing dyes are added to the silver halide emulsion, the sensitizing dye is preferably added during the preparation of the emulsion. When the organic silver salts are introduced in the light-sensitive microcapsule, the emulsion of the organic silver salts can be prepared in the same manner as in the preparation of the silver halide emulsion.

In the preparation of the light-sensitive material, the polymerizable compound is used as the medium for preparation of the liquid composition containing another component of the light-sensitive layer. For example, the silver halide, (including the silver halide emulsion), the reducing agent or the color image forming substance can be dissolved, emulsified or dispersed in the polymerizable compound to prepare the light-sensitive material. Especially, the color image forming substance is preferably incorporated into the polymerizable compound. Further, the necessary components for preparation of a microcapsule, such as shell material can be incorporated into the polymerizable compound.

The light-sensitive composition which is the polymerizable compound containing the silver halide can be prepared using the silver halide emulsion. The light-sensitive composition can be also prepared using silver halide powders which can be prepared by lyophilization. These light-sensitive composition can be obtained by stirring the polymerizable compound and the silver halide using a homogenizer, a blender, a mixer or other conventional stirring device.

Polymers having a principal chain consisting essentially of a hydrocarbon chain substituted in part with hydrophilic groups which contain, in their terminal groups, —OH or nitrogen having a lone electron-pair are preferably introduced into the polymerizable compound prior to the preparation of the light-sensitive composition. The polymer has a function of dispersing silver halide or other component in the polymerizable compound very uniformly as well as a function of keeping thus dispered state. Further, the polymer has another function of gathering silver halide along the interface between the polymerizable compound (i.e., light-sensitive composition) and the aqueous medium in preparation of the microcapsule. Therefore, using this polymer, silver halide can be easily introduced into the shell material of the microcapsule.

The light-sensitive composition can be also prepared by dispersing microcapsule containing silver halide emulsion as a core structure in the polymerizable compound instead of employing the above polymer.

The polymerizable compound (including the light-sensitive composition) is preferably emulsified in an aqueous medium to prepare the coating solution. The necessary components for preparation of the microcapsule, such as shell material can be incorporated into the emulsion. Further, other components such as the reducing agent can be added to the emulsion. The emulsion of the polymerizable compound can be processed for forming shell of the microcapsule.

Examples of the process for preparation of the microcapsules include a process utilizing coacervation of hydrophilic wall-forming materials as described in U.S. Pat. Nos. 2,800,457 and 2,800,458; an interfacial polymerization process as described in U.S. Pat. No. 3,287,154, U.K. Pat. No. 990,443 and Japanese Patent Publication Nos. 38(1963)-19574, 42(1967)-446 and 42(1967)-771; a process utilizing precipitation of polymers as described in U.S. Pat. Nos. 3,418,250 and 3,660,304; a process of using isocyanate-polyol wall materials as described in U.S. Pat. No. 3,796,669; a process of using isocyanate wall materials as described in U.S. Pat. No. 3,914,511; a process of using urea-formaldehyde or urea-formaldehyde-resorcinol wall-forming materials as described in U.S. Pat. Nos. 4,001,140, 4,087,376 and 4,089,802; a process of using melamine-formaldehyde resins hydroxypropyl cellulose or like wall-forming materials as described in U.S. Pat. No. 4,025,455; an in situ process utilizing polymerization of monomers as described in U.K. Pat. No. 867,797 and U.S. Pat. No. 4,001,140; and electrolytic dispersion and cooling process as described in U.K. Pat. Nos. 952,807 and 965,074; a spray-drying process as described in U.S. Pat. No. 3,111,407 and U.K. Pat. No. 930,422; and the like. It is preferable, though not limitative, that the microcapsule is prepared by emulsifying core materials containing the polymerizable compound and forming a polymeric membrane (i.e., shell) over the core materials.

When the emulsion of the polymerizable compound (including the dispersion of the microcapsule) has been prepared by using the light-sensitive composition, the emulsion can be used as the coating solution of the light-sensitive material. The coating solution can also be prepared by mixing the emulsion of the polymerizable compound and the silver halide emulsion. The other components can be added to the coating solution in a similar manner as the emulsion of the polymerizable compound.

There is no specific limitation with respect to the addition of the base precursor in the preparation of the light-sensitive material.

The light-sensitive material of the invention can be prepared by coating and drying the above-prepared coating solution on a support. The process for coating the coating solution on a support can be easily carried out in the conventional manner.

Use of the light-sensitive material is described below.

In the use of the light-sensitive material of the invention, a development process is conducted simultaneously with or after an imagewise exposure.

Various exposure means can be employed in the imagewise exposure, and in general, the latent image on the silver halide is obtained by imagewise exposure to radiation including visible light. The type of light source and exposure can be selected depending on the light-sensitive wavelengths (sensitized wavelength when seinsitization is carried out) or sensitivity of silver halide. Original image can be either monochromatic image or color image.

Development of the light-sensitive material can be conducted simultaneously with or after the image exposure. The development can be conducted using a developing solution in the same manner as the image forming method described in Japanese Patent Publication No. 45(1970)-11149. The image forming method described in Japanese Patent Provisional Publication No. 61(1986)-69062 which employs a heat development process has an advantage of simple procedures and short processing time because of the dry process. Thus, the latter method is preferred as the development process of the light-sensitive material.

Heating in the heat-development process can be conducted in various known manners. The heating layer which is arranged on the light-sensitive material can be used as the heating means in the same manner as the light-sensitive material described in Japanese Patent Provisional Publication No. 61(1986)-294434. The light-sensitive material is preferably heated while suppressing supply of oxygen into the light-sensitive layer from outside. Heating temperature for the development process usually ranges from 80° C. to 200° C., and preferably from 100° C. to 160° C. Various heating patterns are applicable. The heating time is usually not shorter than 1 second, preferably from 1 second to 5 minutes, and more preferably from 1 second to 1 minute.

During the above development process, a polymerizable compound within the area where a latent image of the silver halide has been formed or within the area where a latent image of the silver halide has not been formed is polymerized. In a general system, the polymerizable compound within the area where the latent image has been formed is polymerized. If a nature or amount of the reducing agent is controlled, the polymerizable compound within the area where the latent image has not been formed can be polymerized.

A polymer image can be formed on the light-sensitive layer in the above process. A color image can be obtained by fixing a dye or pigment on a polymer image.

Further, a color image can be formed on the light-sensitive material in which the light-sensitive layer contains a color former and a developer, one of them is together with the polymerizable compound contained in a microcapsule, and the other is arranged outside of the microcapsule.

The image can be also formed on the image-receiving material. The image-receiving material is described hereinbelow.

Examples of the material employable as the support of the image-receiving material include baryta paper in addition to various examples which can be employed as the support of the known light-sensitive materia. In the case that a porous material, such as paper is employed as the support of the image-receiving material, the porous support preferably has such a surface characteristic that a filtered maximum waviness of not less than 4 $\mu$m is observed in not more than 20 positions among 100 positions which are determined at random on a filtered waviness curve obtained according to JIS-B-0610. Further, a transparent material can be employed as the support of the image-receiving material to obtain a transparent or a projected image.

The image-receiving material is usually prepared by providing an image-receiving layer on the support. The image-receiving layer can be constructed according to the color formation system. In the cases that a polymer image is formed on the image-receiving material and that a dye or pigment is employed as the color image forming substance, the image-receiving material can be composed of a simple support.

For example, when a color formation system using a color former and developer is employed, the developer can be contained in the image-receiving layer. Further, the image-receiving layer can be composed of at least one layer containing a mordant. The mordant can be selected from the compounds known in the art of the conventional photography according to the kind of the color image forming substance. If desired, the image-receiving layer can be composed of two or more layers containing two or more mordants different in the mordanting power from each other.

The image-receiving layer preferably contains a polymer as binder. The binder which may be employed in the above-mentioned light-receiving layer is also employable in the image-receiving layer. Further, a polymer having a transmission coefficient of oxygen of not more than $1.0\times10^{-11}$ $cm^3.cm/cm^2.sec.cmHg$ can be used as the binder to protect the color of the image formed on the image-receiving material.

The image-receiving layer can contain a granulated thermoplastic compound to obtain a glossy image. There is no specific limitation with respect to the thermoplastic compound. The thermoplastic compound include known plastic resin and wax. The thermoplastic resin preferably has a glass transition temperature of not more than 200° C. The wax preferably has a melting point of not more than 200° C.

A photopolymerization initiator or a thermalpolymerization initiator can be contained in the image-receiving layer to polymerize the transferred unpolymerized polymerizable compound, so that the obtained image is fixed on the image-receiving layer.

A dye or pigment can be contained in the image-receiving layer for the purpose of entering letters, symbols, frames etc. in the image-receiving layer, or of giving a certain color to the background of the image. Further, the dye or pigment can be also employed for the purpose of making it easy to distinguish the sides of the image-receiving material. In the case that it is possible that the dye or pigment disturbs the image formed on the image-receiving layer, it is preferred that the density of the dye or pigment is low (e.g. reflection density of not higher than 1), or the dye or pigment has a property of being decolored when it is heated or irradiated with light.

Further, when a white pigment, such as titanium dioxide, barium sulfate etc. is contained in the image-receiving layer, the image-receiving layer can function as a white reflection layer. In this case, the white pigment is used in an amount of from 10 g to 100 g based on 1 g of the thermoplastic material.

The above-mentioned dye and pigment can be either uniformly or locally contained in the image-receiving layer. For example, when the support is composed of transparent material, the white pigment can be partially contained in the image-receiving layer to make a part of a reflection image to be transparent. Thus, information of the image which is unnecessary in a transparent image can be entered in the part of the image-receiving layer containing the white pigment as the reflection image.

The image-receiving layer can be composed of two or more layers according to the above-mentioned functions. The thickness of the image-receiving layer preferably ranges from 1 to 100 $\mu$m, more preferably from 1 to 20 $\mu$m.

A protective layer can be provided on the surface of the image-receiving layer. A layer containing a granulated thermoplastic compound can be also provided on the image-receiving layer.

A layer containing an adhesive and a release paper can be provided in the order on the support of the image-receiving material on the opposite side of the image-receiving layer.

After the development process, pressing the light-sensitive material on the image-receiving material to transfer the unpolymerized polymerizable compound to the image-receiving material, a polymer image can be obtained in the image-receiving material. The process for pressing can be carried out in various known manners.

In the case that the light-sensitive layer contains a color image forming substance, the color image forming substance is fixed by polymerization of the polymerizable compound. Then, pressing the light-sensitive material on the image-receiving material to transfer the color image forming substance in unfixed portion, a color image can be produced on the image-receiving material.

After the image is formed on the image-receiving material, the image-receiving material can be heated to polymerize the transferred unpolymerized polymerizable compound. By the above-mentioned process, the obtained image can be improved in the preservability.

Various image recording apparatus can be used for the image-forming method. An example of the apparatus comprises an exposure device for imagewize exposing the light-sensitive material to form a latent image, a heat development device for fixing the area corresponding to the latent image, a transfer device for pressing the developed light-sensitive material on the image-receiving material. Another example of the apparatus comprises an fixing apparatus for irradiating with light, pressing or heating the image-receiving material on which an image has been transferred in addition to the above-mentioned devices.

The light-sensitive material can be used for monochromatic or color photography, printing, radiography, diagnosis (e.g., CRT photography of diagnostic device using supersonic wave), copy (e.g., computer-graphic hard copy), etc.

The present invention is further described by the following examples without limiting the invention thereto.

EXAMPLE 1

In 80 g of 3% aqueous solution of polyvinyl alcohol was dispersed 20 g of the following base precursor (7) using a Dynomill dispersing device to obtain a dispersion. A coating solution was prepared from 37 g of the obtained solid dispersion of the base precursor, 22 g of an aqueous solution of 5% polyvinyl alcohol and 11 g of water. The coating solution was coated on a polyethylene terephthalate film using a wire bar of #40 and dried at 40° C. for 30 minutes to prepare a coated sample of the base precursor (7). The sample was heated on a hot plate at 125° C. After a lapse of a given time, the sample was taken out and the pH on the surface of the film was measured. Further, the experiment was carried out by changing the heating temperature to 100° C., 125° C., 140° C. and 150° C. The pH was measured at every ten records. The results of the measurements are shown in FIG. 1. FIG. 1 is a graph showing the relationship between the time and the pH obtained by plotting them. In FIG. 1, the abscissa axis represents the time and the ordinate represents the pH.

(Base precursor (7))

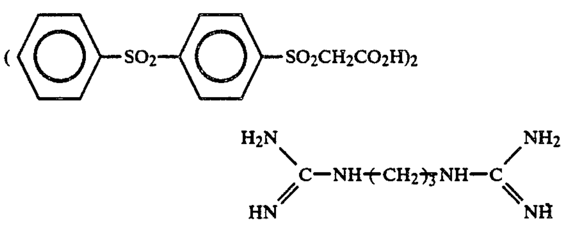

EXAMPLE 2

The procedure of Example 1 was repeated except that each 20 g of the following base precursors (1), (2), (6), (9), (15), (16), (17) was respectively used in place of 20 g of the base precursor (7) to prepare coated samples of the base precursors (1), (2), (6), (9), (15), (16) and (17). In a similar manner to that described in Example 1, changes in the pH on the surface of the film upon heating were measured. The results of the measurements are shown in FIGS. 2 to 8.

(Base precursor (1))

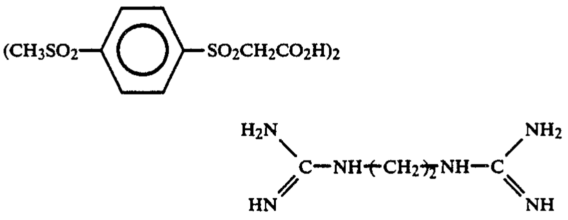

(Base precursor (2))

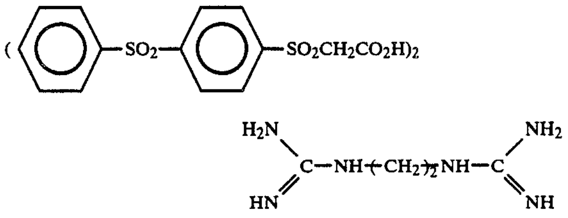

(Base precursor (6))

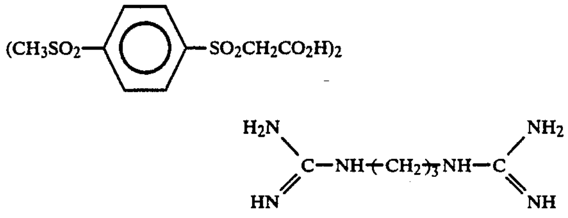

(Base precursor (9))

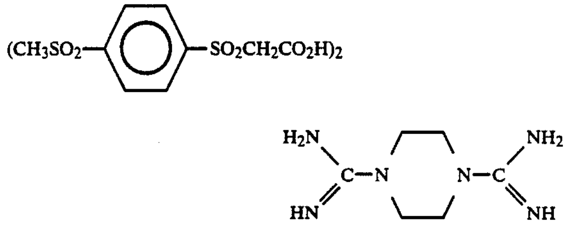

(Base precursor (15))

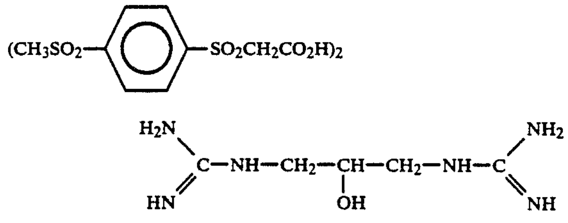

-continued (Base precursor (16))

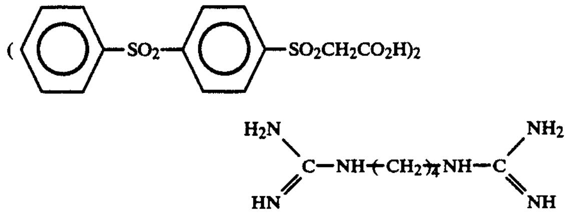

(Base precursor (17))

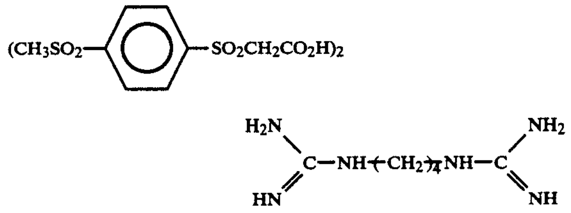

COMPARISON EXAMPLE 1

The procedure of Example 1 was repeated except that each 20 g of the following base precursors (X) and (Y) was used in place of 20 g of the base precursor (7) to prepare coated samples of the base precursors (X) and (Y).

Figure 9:
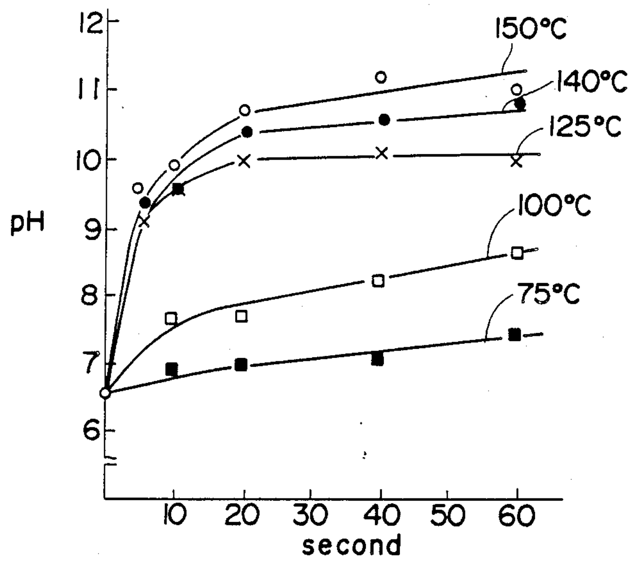
Figure 10:
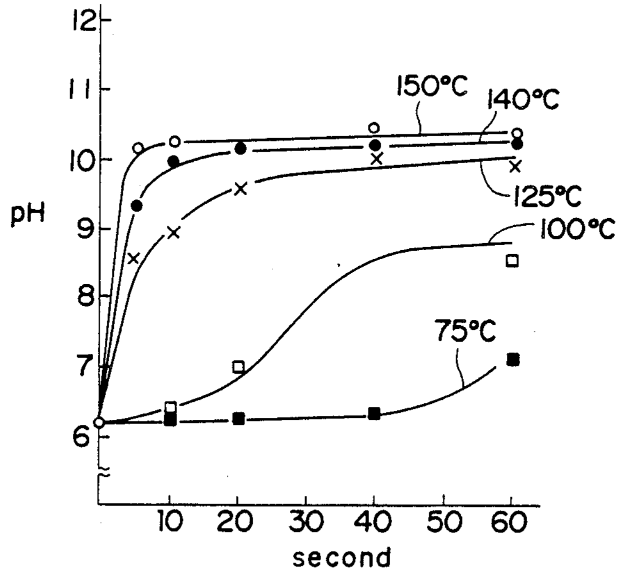

In a similar manner to that described in Example 1, changes in the pH on the surface of the film upon heating and heating at 75° C. were measured. The results are shown in FIGS. 9 and 10.

(Base precursor (X))

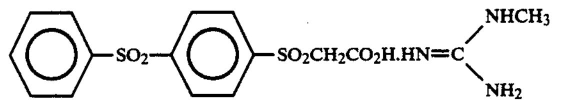

(Base precursor (Y))

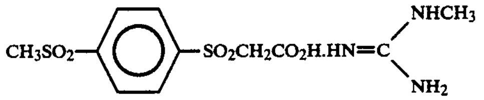

It is apparent from the results of FIGS. 1 to 10 that each of the base precursors of the present invention rapidly releases a base when it is heated to 140° C. or higher, but they do not release a base even when it is heated at 100° C. or lower for a long time. The conventional base precursors (X) and (Y) release a base slowly even at a temperature of 125° C. and it gradually release the base at a low temperature. When the structure of the base precursor (X) is compared with those of the base precursors (2) and (7) of the present invention, the base precursor (X) is a salt of a monoacidic base having a similar structure to those of the base precursors (2) and (7) with the same acid as those of the base precursors (2) and (7). When the structure of the base precursor (Y) is compared with those of the base precursors (1) and (6) of the present invention, the base precursor (Y) is a salt of a monoacidic base having a similar structure to those of the base precursors (1) and (6) with the same acid as those of the base precursors (1) and (6). Accordingly, it can be understood that the decomposition behavior of a base precursor against temperature is greatly changed by replacing a monoacidic base with a diacidic base.

EXAMPLE 3

Figure 11:
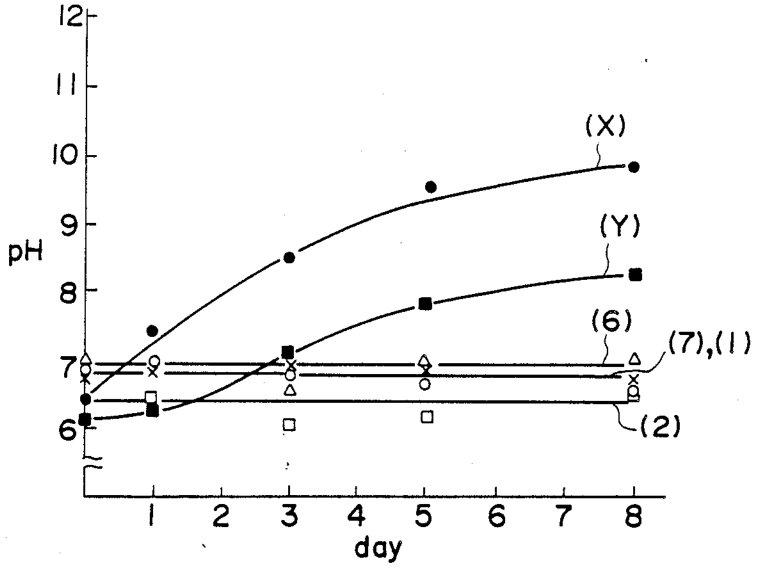
FIG. 11 is a graph showing the results of the measurements of changes in the pH of the samples during storage, wherein the abscissa axis represents the storage time and the ordinate axis represents the pH.

The coated sample of the base precursor (7) prepared in Example 1 was placed in a box made of a metal, sealed and stored at 50° C. After a lapse of a given period of time, the sample was taken out and the pH on the surface of the film was measured. The results of the measurements are shown in FIG. 11. FIG. 11 is a graph showing the relationship between the pH and the storage time obtained by plotting them on the basis of the measurement results. In FIG. 11, the abscissa axis represents the storage time and the ordinate axis represents the pH.

EXAMPLE 4

The coated samples of the base precursors (1), (2) and (6) prepared in Example 2 was stored in a similar manner to that described in Example 3, and the pH on the surface of the film was measured. The results of the measurements together with those of Example 3 are shown in FIG. 11.

COMPARISON EXAMPLE 2

Each of the coated samples of the base precursors (X) and (Y) prepared in Comparison Example 1 was stored in a similar manner to that described in Example 3, and the pH on the surface of the film was measured. The results of the measurements together with those of Example 3 are shown in FIG. 11.

It is apparent from the results of FIG. 11 that the base precursors of the present invention do not release any base under storage conditions at 50° C., while the conventional base precursors (X) and (Y) release considerable amounts of bases for a storage time of only 8 days at 50° C.

EXAMPLE 5

Figure 12:
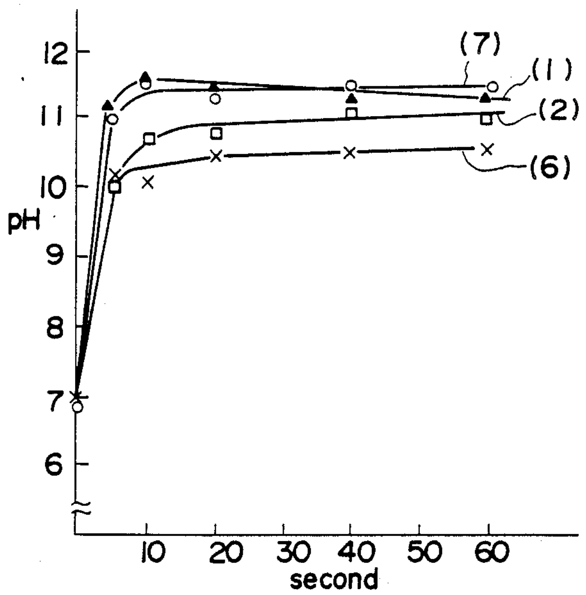
FIG. 12 is a graph showing the results of the measurements of changes in the pH of the samples during heating after storage, wherein the abscissa axis represents the heating time and the ordinate axis represents the pH.

The coated sample of the base precursor (3) prepared in Example 2 was stored under the storage conditions of Example 3 for 8 days and then heated to 150° C. on a hot plate. After a lapse of a given time, the sample was taken out and the pH on the surface of the film was measured. The results of the measurements are shown in FIG. 12. FIG. 12 is a graph showing the relationship between the time and the pH obtained by plotting them on the basis of the measurement results. In FIG. 12, the abscissa axis represents the time and the ordinate axis represents the pH.

EXAMPLE 6

Each of the coated samples of the base precursors (1), (2) and (6) prepared in Example 1 was stored under the storage conditions of Example 3 for 8 days and then heated to 150° C. on a hot plate. After a lapse of a given time, the sample was taken out and the pH on the surface of the film was measured. The results of the measurements together with those of Example 5 are shown in FIG. 12.

It is apparent from the results of FIG. 12 that the base precursors of the present invention hardly cause a lowering of base-forming function when they are heated, even after they are stored under severe conditions for a long time.

EXAMPLE 7

Preparation of silver halide emulsion

In 1,200 ml of water were dissolved 24 g of gelatin and 1.2 g of sodium chloride, and the resulting gelatin solution was kept at 60° C. The gelatin solution was adjusted to pH of 3.2 using 1N sulfric acid. To the gelatin solution, 600 ml of an aqueous solution containing 117 g of potassium bromide and 600 ml of an aqueous solution containing 0.74 mole of silver nitrate were added simultaneously at the same feed rate over a period of 15 minutes. After 5 minutes, to the resulting mixture was added 200 ml of an aqueous solution containing 4.3 g of potassium iodide at the same feed rate over 5 minutes. To the dispersion was added 1.2 g of poly(isobutyleneco-sodium meleinate) and sedimentated the silver halide. After washing for desalting the emulsion, in the emulsion was dissolved 24 g of gelatin. To the resulting emulsion were added 5 mg of thiosulfate chloride and 0.47 g of the following sensitizing dye, and then was chemical sensitized at 60° C. for 15 minutes to obtain a silver halide emulsion (I). Yield of the emulsion was 1,000 g.

(Sensitizing dye)

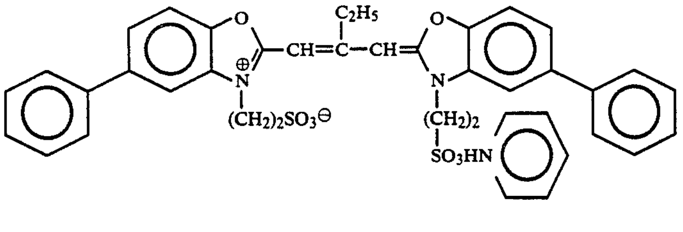

Preparation of light-sensitive composition

In 100 g of the following polymerizable compound (Kayarad R-604; produced by Nippon Kayaku Co., Ltd.) were dissolved 1.6 g of the following copolymer, 20.0 g of Pargascript Red I-6-B (tradename of Ciba-Geigy) and 0.43 g of p-toluene sulfoneamide.

(Polymerizable compound)

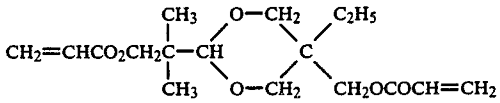

(Copolymer)

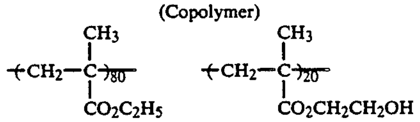

To 90.0 g of the solution were added 6.10 g of the following developing agent (reducing agent), 6.45 g of the following hydrazine derivative (reducing agent), 0.00875 g of the following antifogging agent, 1.8 g of Emulex NP-8 (tradename of Nippon Emulsion Co., Ltd.) and 20.0 g of methylene chloride. The resulting mixture was made uniform.

(Developing agent)

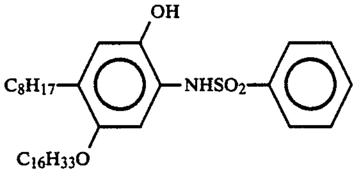

(Hydrazine derivative)

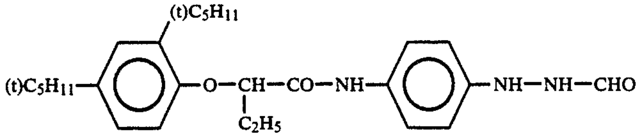

(Antifogging agent)

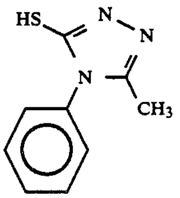

To 10.0 g of the silver halide emulsion (I) was added 10% aqueous solution of potassium bromide, and the mixture was stirred for 5 minutes. The obtained mixture was added to thhe above uniform solution, and the mixture was stirred at 15,000 r.p.m. for 5 minutes using homogenizer keeping the temperature at 25° C. to obtain a light-sensitive composition in the form of a W/O emulsion.

Preparation of light-sensitive microcapsule

Using 20% aqueous solution of phosphoric acid, 208 g of 10% aqueous solution of a partial sodium salt of polyvinylbenzene sulfonic acid (tradename VERSA TL 500 produced by National Starch, Co.) was adjusted to pH of 3.5. To the W/O emulsion was added 4.5 g of an adduct of xylylene diisocyanate and trimethylolpropane (Takenate 110N produced by Takeda Chemical Industries, Ltd.), and the resulting W/O emulsion was added to the aqueous solution of the partial sodium salt of polyvinylbenzene sulfonic acid. The resulting mixture was stirred at 7,000 r.p.m. for 30 minutes using homogenizer at 40° C. to obtain W/O/W emulsion.

Separately, to 40.35 g of distilled water were added 7.5 of melamine and 12.35 g of 37% aqueous solution of formaldehyde, and the mixture was stirred for 30 minutes at 60° C. to give a transparent melamine-formaldehyde precondensate.

The obtained precondensate was added to the W/O/W emulsion at 25° C. The mixture was then adjusted to pH 6.0 using 20% aqueous solution of phosphoric acid, and then was stirred for 90 minutes at 60° C.

Further, to the resulting mixture was added 27 g of 40% aqueous solution of urea and the mixture was adjusted to pH 3.5 using 20% aqueous solution of phosphoric acid. The resulting mixture was then heated at 60° C. and stirred for 40 minutes. After cooling to room temperature, the mixture was adjusted to pH 7.0 using 10% aqueous solution of sodium hydroxyde to obtain a dispersion containing a light-sensitive microcapsule having a shell material comprising melamine-formaldehyde resin.

Preparation of solid dispersion of base precursor

To 160 g of 3% aqueous solution of polyvinyl alcohol was dispersed 40 g of the above described base precursor (1) to obtain 20% dispersion (1) of solid particles of the base precursor (1).

Dispersions (2), (6), (7), (9), (15), (16) and (17) of solid particles of the base precursors (2), (6), (7), (9), (15), (16) and (17) were respectively prepared in the same manner as described above.

Preparation of light-sensitive material

To 30.0 g of the microcapsule dispersion were added 11.3 g of the dispersion (1) of solid particles of the base precusor (1), 4.0 g of 20% solution (solvent: water/ethanol =50/50 as volume ratio) of the following hot-melt solvent, 6.0 g of 20% aqueous solution of sorbitol, 10.0 g of 20% aqueous dispersion of corn starch, 4.0 g of 5% aqueous solution of Emulex NP-8 (tradename of Nippon Emulsion Co., Ltd.) and distilled water to obtain 88 ml of a coating solution. The coating solution was coated on a polyethylene terephthalate film having a thickness of 100 μm using a wire bar of #40 in an coating amount of 63 ml/m$^2$ and dried for 30 minutes at 60° C. to obtain a light-sensitive material (A).

Light-sensitive materials (B) to (H) were prepared in the same manner as described above, except that the dispersions (2), (6), (7), (9), (15), (16) and (17) were respectively used in place of 11.3 g of the dispersion (1) and the amount of the dispersion was changed as shown in Table 1.

Dispersions (43) and (44) of solid particles of the following base precursors (43) and (44) were respectively prepared in the same manner as described above.

Light-sensitive materials (I) and (J) were prepared in the same manner as described above, except that the dispersions (43) and (44) were respectively used in place of 11.3 g of the dispersion (1) and the amount of the dispersion was changed as shown in Table 1.

(Base precursor (43))

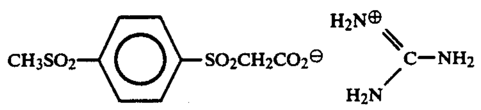

(described in Japanese Patent Provisional Publication No. 60(1985)-237443)

(Base precursor (44))

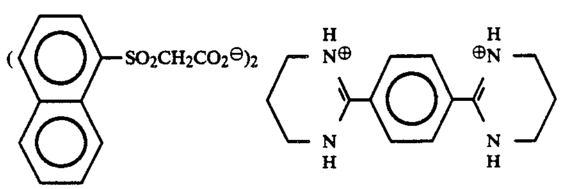

(described in Japanese Patent Application No. 62(1987)-237443)

Preparation of image-receiving material

To 125 g of water was added 11 g of 40% aqueous solution of sodium hexametaphosphate, and were further added 34 g of zinc 3,5-di-α-methylbenzylsalicylate and 82 g of 55% slurry of calcium carbonate, followed by coarsely dispersing in a mixer. The coarse dispersion was then finely dispersed in Dynomill dispersing device. To 200 g of the resulting dispersion were added 6 g of 50% latex of SBR (styrene-butadiene rubber) and 55 g of 8% aqueous solution of polyvinyl alcohol, and the resulting mixture was made uniform. The mixture was coated on a baryta paper having basis weight of 43 g/m$^2$ to give a layer having wet thickness of 30 μm and dried dried to obtain an image-receiving material.

Evaluation of light-sensitive material

Each of the light-sensitive materials (A) to (H) prepared in Example 7 according to the present invention and the light-sensitive materials (I) and (J) for comparison was imagewise exposed to light using a tungsten lamp at 2,000 lux for 1 second through a filter in which the density was continuously changing from 0 to 3.0, and then heated on a hot plate at 150° C. for 10 seconds. Each of the exposed and heated light-sensitive materials was then combined with the image-receiving material and passed through press rolls at pressure of 500 kg/cm$^2$. The density of the obtained magenta positive image on the image-receiving material was measured using Macbeth's reflection densitometer.

Separately, each of the light-sensitive materials was left at ordinary temperature (25° C.) in the low humidity (15%) and was left for 7 days, or was sealed in a metal box and was left at temperature of 50° C. for 7 days. The image was formed on the image-receiving material in the same manner as described above. The density of the obtained magenta positive image on the image-receiving material was measured using Macbeth's reflection densitometer.

The results are set forth in Table 1. In Table 1, "Dmax" means the maximum density and "Dmin" means the minimum density.

TABLE 1

| Light-sensitive Material | Base Precursor | Amount | Immediately after Preparation Dmax | Dmin | After 7 days at 25° C./15% Dmax | Dmin | After 7 days at 50° C. Dmax | Dmin |
|---|---|---|---|---|---|---|---|---|
| (A) | (1) | 11.3 g | 1.31 | 0.18 | 1.22 | 0.21 | 1.30 | 0.18 |
| (B) | (2) | 13.3 g | 1.41 | 0.14 | 1.37 | 0.16 | 1.40 | 0.16 |
| (C) | (6) | 11.5 g | 1.39 | 0.26 | 1.28 | 0.21 | 1.38 | 0.26 |
| (D) | (7) | 13.5 g | 1.47 | 0.13 | 1.39 | 0.17 | 1.42 | 0.12 |
| (E) | (9) | 11.7 g | 1.41 | 0.38 | 1.40 | 0.45 | 1.41 | 0.40 |
| (F) | (15) | 11.8 g | 1.44 | 0.29 | 1.38 | 0.31 | 1.37 | 0.28 |
| (G) | (16) | 13.8 g | 1.45 | 0.32 | 1.45 | 0.37 | 1.45 | 0.33 |
| (H) | (17) | 11.8 g | 1.43 | 0.17 | 1.37 | 0.20 | 1.39 | 0.19 |
| (I) | (43) | 12.9 g | 1.12 | 0.21 | 1.09 | 0.24 | 1.08 | 0.74 |
| (J) | (44) | 12.0 g | 1.34 | 0.58 | 1.27 | 0.84 | 1.30 | 0.61 |

Further, on the surface of each of the light-sensitive material was dropped 20 μl of distilled water immediately after preparation, or after storage for 7 days at 50° C. Then, pH at the surface of the light-sensitive materials was measured using a plane pH electrode.

The results are set forth in Table 2.

TABLE 2

| Light-sensitive Material | pH on Surface: Immediately after Preparation | After Storage for 7 days at 50° C. |
|---|---|---|
| (A) | 6.29 | 6.31 |
| (B) | 6.46 | 6.50 |
| (C) | 6.37 | 6.41 |
| (D) | 6.48 | 6.50 |
| (E) | 6.33 | 6.27 |
| (F) | 6.18 | 6.19 |
| (G) | 6.79 | 6.81 |
| (H) | 7.02 | 7.03 |
| (I) | 6.30 | 8.14 |
| (J) | 6.35 | 6.34 |

It is apparent from the results in Table 1 that the light-sensitive materials of the present invention can give a clear image having a high contrast, even after they are stored under severe conditions.

It is also apparent from the results in Table 2 that even if the light-sensitive materials of the present invention are stored under severe conditions, a base is scarcely released from the base precusor.

The light-sensitive material (I) for comparison release a hydrophilic guanidine as a base (similarly to the present invention) and can give a clear image after storage at an ordinary temperature and the low humidity. However, after storage at a high temperature, the pH on the surface of the light-sensitive material (I) increases as shown in Table 2. Thus, the light-sensitive material (I) gives an image having a low contrast when it is stored under severe conditions.

Further, the light-sensitive material (J) for comparison releases a hydrophobic base, and can not accelerate the development when it is heated at 150° C. for 10 seconds. Accordingly, the light-sensitive material (J) gave an image having a low contrast. After the material (J) is stored under severe conditions, the contrast of the image further decreases.

It is apparent form the above-mentioned results that the light-sensitive material employing the base precusor of the present invention can give a clear image having a high contrast, even after it is stored under severe conditions.

We claim:

1. A process for formation of a base comprising the step of heating a base precursor in the form of a salt of an organic base with a carboxylic acid which has such a property that the carboxyl group of the acid undergoes decarboxylation at a temperature of 50° to 200° C., wherein the organic base is a diacidic to tetraacidic base having the following formula (II):

$$R^6(-B)_n \qquad (II)$$

wherein $R^6$ is an n-valent residue of a hydrocarbon or a heterocyclic ring, the number of the carbon atoms contained in the organic base is not more than six times the number of the guanidine moieties, "n" is an integer of 2 to 4, and "B" is a monovalent group corresponding to an atomic group formed by removing one hydrogen atom from a compound having the following formula (I):

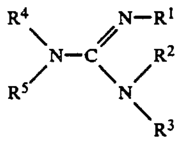

(I)

wherein each of $R^1$, $R^2$, $R^3$, $R^4$ and $R^5$ independently is a monovalent group selected from the group consisting of hydrogen, an alkyl group, an alkenyl group, an alkynyl group, a cycloalkyl group, an aralkyl group, an aryl group and a heterocyclic group, each of which may have one or more substituent groups, and any two of $R^1$, $R^2$, $R^3$, $R^4$ and $R^5$ may be combined together to form a five-membered or six-membered nitrogen-containing heterocyclic ring.

2. The process as claimed in claim 1, wherein the base precursor is heated at a temperature of 80° to 250° C.

3. The process as claimed in claim 1, wherein the base precursor is heated the presence of a polymer.

4. The process as claimed in claim 1, wherein each of $R^1$ to $R^5$ in the formula (I) is hydrogen or an alkyl group.

5. The process as claimed in claim 1, wherein the compound having the formula (I) is guanidine.

6. The process as claimed in claim 1, wherein the number of carbon atoms contained in the organic base is not more than five times the number of the guanidine moieties.

7. The process as claimed in claim 1, wherein the organic base has a symmetrical chemical structure.

8. The process as claimed in claim 1, wherein the number of the guanidine moieties is 2.

9. The process as claimed in claim 1, wherein $R^6$ in the formula (II) is an alkylene group or an arylene group, which may have one or more substituent groups.

10. The process as claimed in claim 1, wherein the carboxylic acid has an aryl group or an arylene group.

11. The process as claimed in claim 1, wherein the carboxylic acid has the following formula (III-I):

$$Y(-SO_2-\overset{\displaystyle R^{31}}{\underset{\displaystyle R^{32}}{\overset{|}{\underset{|}{C}}}}-CO_2H)_k \qquad \text{(III-1)}$$

wherein each of $R^{31}$ and $R^{32}$ independently is a monovalent group selected from the group consisting of hydrogen, an alkyl group, an alkenyl group, a cycloalkyl group, an aralkyl group, an aryl group and a heterocyclic group, each of which may have one or more substituent groups, "k" is 1 or 2; provided that when "k" is 1, Y is a monovalent group selected from the group consisting of an alkyl group, a cycloalkyl group, an alkenyl group, an alkynyl group, an aralkyl group, an aryl group and a heterocyclic group, each of which may have one or more substituent groups, and when "k" is 2, "Y" is a divalent group selected from the group consisting of an alkylene group, an arylene group and a heterocyclic group, each of which may have one or more substituent groups.

12. The process as claimed in claim 1, wherein the salt of the organic base with the carboxylic acid has a melting point of 50° to 200° C.

* * * * *